(12) United States Patent
McCarthy et al.

(10) Patent No.: US 8,927,575 B2
(45) Date of Patent: Jan. 6, 2015

(54) SALTS AND SOLVATES OF A TETRAHYDROISOQUINOLINE DERIVATIVE

(71) Applicant: Spinifex Pharmaceuticals Pty Ltd, South Yarra, Victoria (AU)

(72) Inventors: Thomas David McCarthy, Malvern East (AU); Craig James Stewart Boyle, Swavesey (GB); Alexander Redvers Eberlin, Cambridge (GB); Peter Michael Kelly, Kelburn (NZ)

(73) Assignee: Spinifex Pharmaceuticals Pty Ltd, Preston, Victoria (AU)

( * ) Notice: Subject to any disclaimer, the term of this patent is extended or adjusted under 35 U.S.C. 154(b) by 0 days.

(21) Appl. No.: 14/083,391

(22) Filed: Nov. 18, 2013

(65) Prior Publication Data

US 2014/0080865 A1  Mar. 20, 2014

Related U.S. Application Data

(62) Division of application No. 13/187,882, filed on Jul. 21, 2011, now Pat. No. 8,614,227.

(60) Provisional application No. 61/366,367, filed on Jul. 21, 2010.

(51) Int. Cl.
*C07D 217/26* (2006.01)
*A61K 31/47* (2006.01)

(52) U.S. Cl.
CPC .............. *C07D 217/26* (2013.01); *A61K 31/47* (2013.01)
USPC .......................................... 514/307; 546/147

(58) Field of Classification Search
None
See application file for complete search history.

(56) References Cited

U.S. PATENT DOCUMENTS

| | | | |
|---|---|---|---|
| 5,236,934 | A | 8/1993 | Van Atten et al. |
| 5,246,943 | A | 9/1993 | Blankley et al. |
| 7,795,275 | B2 | 9/2010 | Smith et al. |

FOREIGN PATENT DOCUMENTS

| | | |
|---|---|---|
| WO | 2006/066361 | 6/2006 |
| WO | 2007/106938 | 9/2007 |
| WO | 2011/088504 | 7/2011 |

OTHER PUBLICATIONS

Klutchko, et al. (1994): Tetrahydroisoquinoline derivatives wit AT2-specific angiotensis II receptor binding inhibitory activity; Bioorganic & Medical Chemistry Letters; vol. 4, No. 1, pp. 57-62.
Wexler, et al., (1996), J. Med. Chem., 39(3), p. 625-656.
Van Atten, et al., "A Novel Series of Selective, Non-Peptide Inhibitors of Angiotensin II Binding to the AT20 Site," J. Med. Chem. (1993), 36(25) pp. 3985-3992.
PCT/GB2011/001096 International Search Report mailed Aug. 29, 2011 and Written Opinion.
PCT/GB2011/001096 International Preliminary Report on Patentability mailed Jan. 31, 2011.
Chinese Search Report Application No. 201180035468.9, (2011).

*Primary Examiner* — Zinna Northington Davis
(74) *Attorney, Agent, or Firm* — Wolff IP, a Prof. Corp.; Jennifer R. Wolff

(57) ABSTRACT

(S)-2-(Diphenylacetyl)-1,2,3,4-tetrahydro-6-methoxy-5-(phenylmethoxy)-3-isoquinoline carboxylic acid in substantially pure form is described together with its sodium salt and solvates. Methods for preparing the compound, its sodium salt and its solvates and pharmaceutical compositions comprising them are also described.

11 Claims, 10 Drawing Sheets

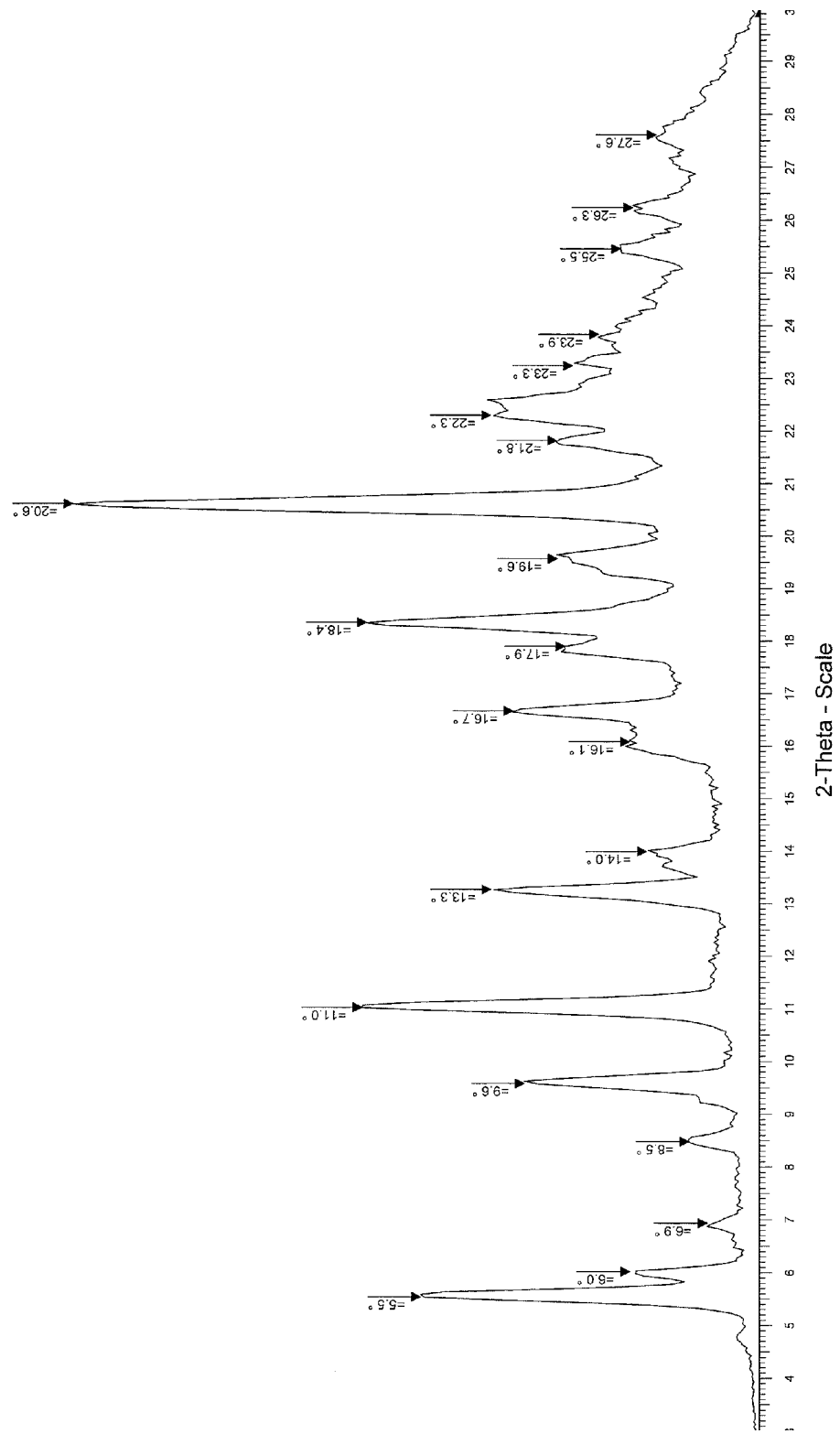
FIGURE: 1 COMPOUND 2 (FROM ACETONITITRILE)

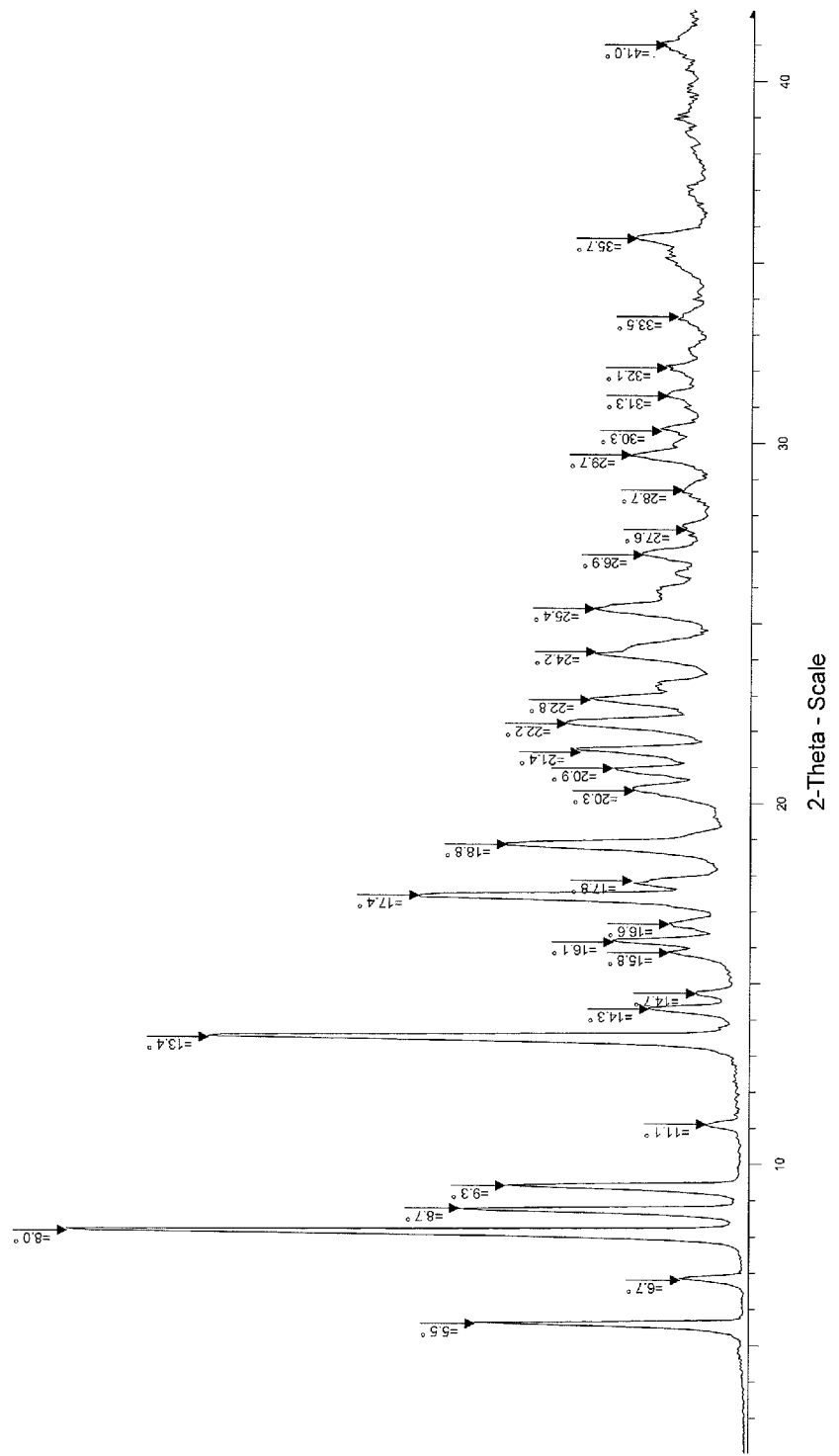
FIGURE: 2 COMPOUND 4

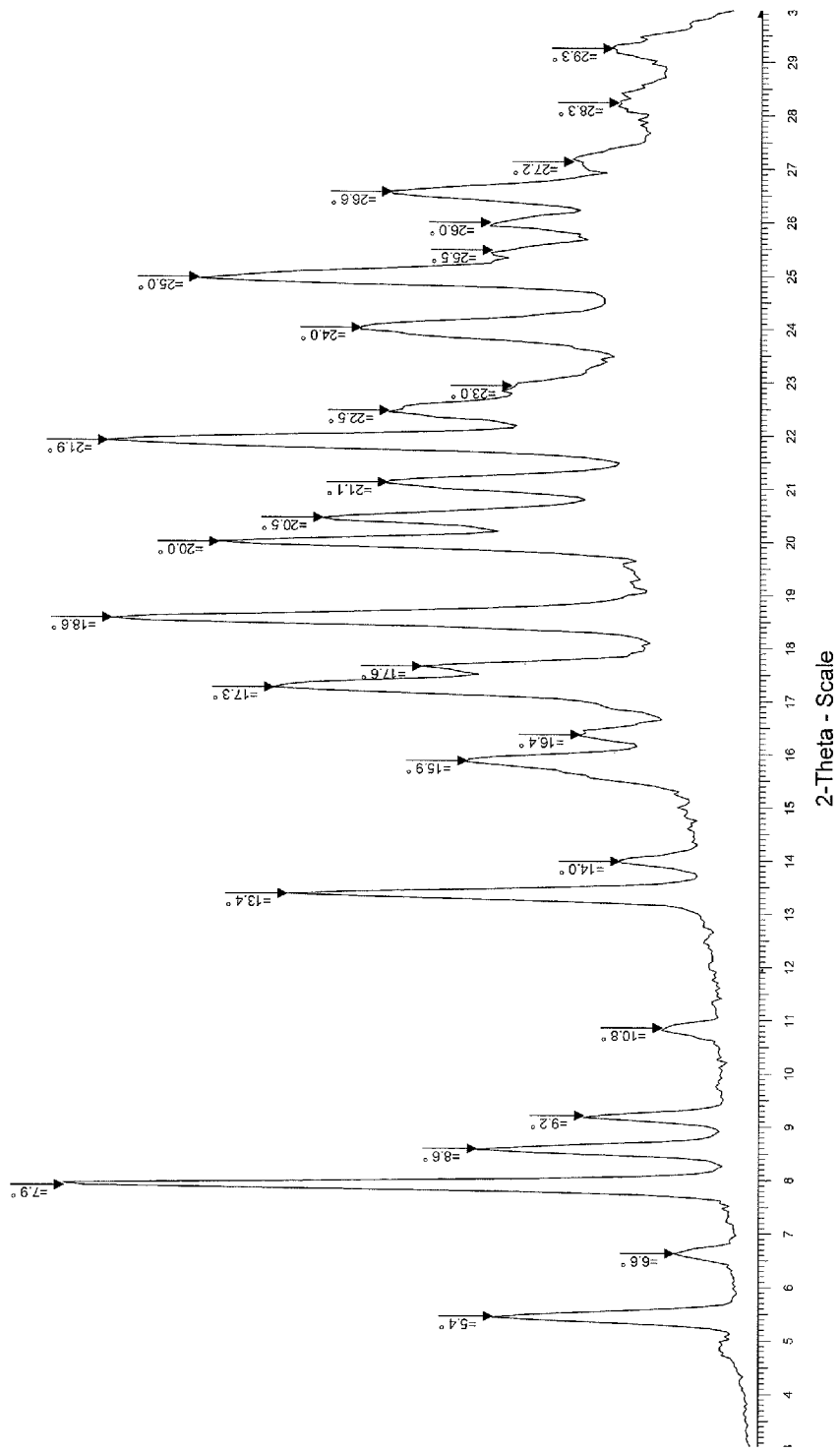
FIGURE 3: COMPOUND 5

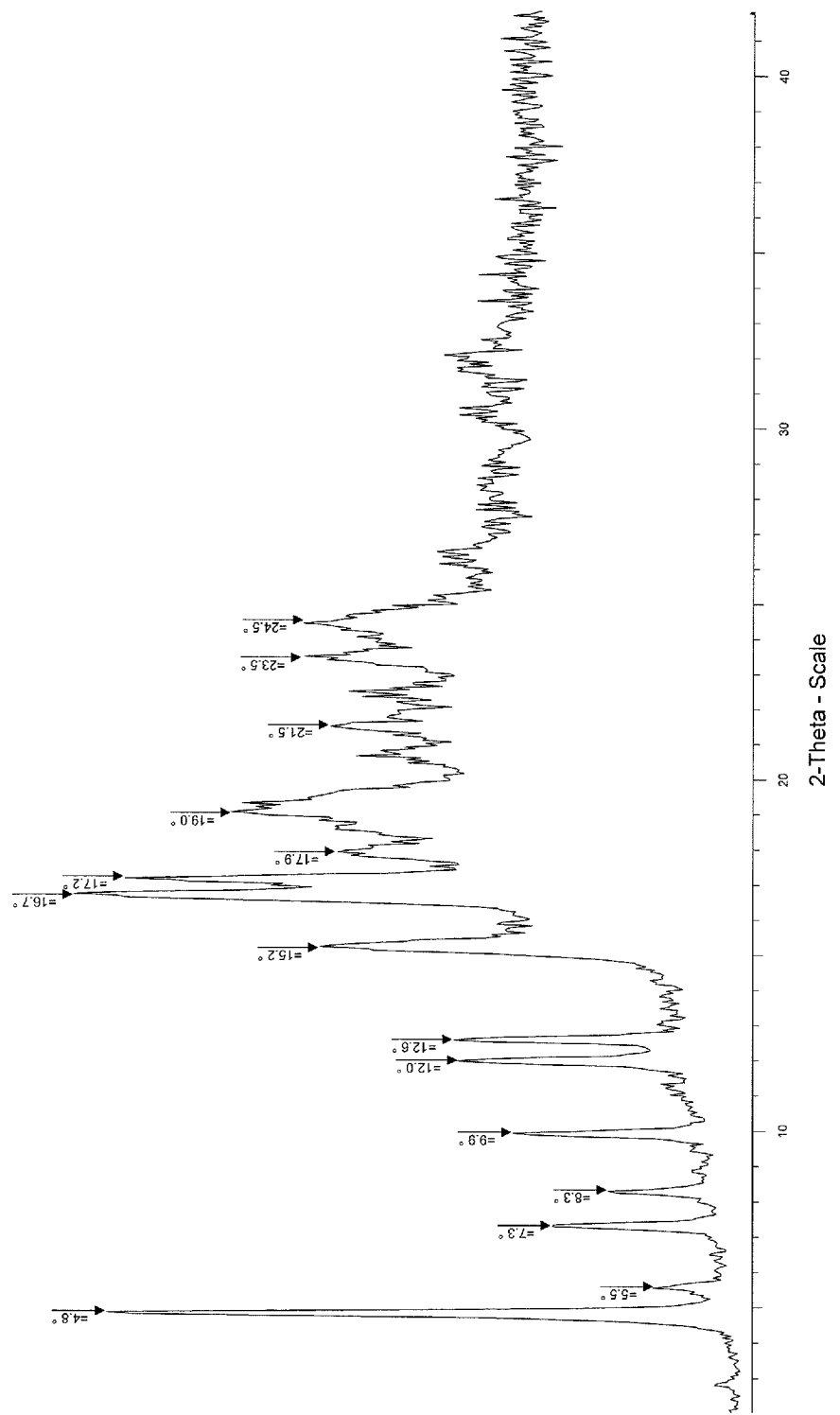
FIGURE: 4 COMPOUND 6

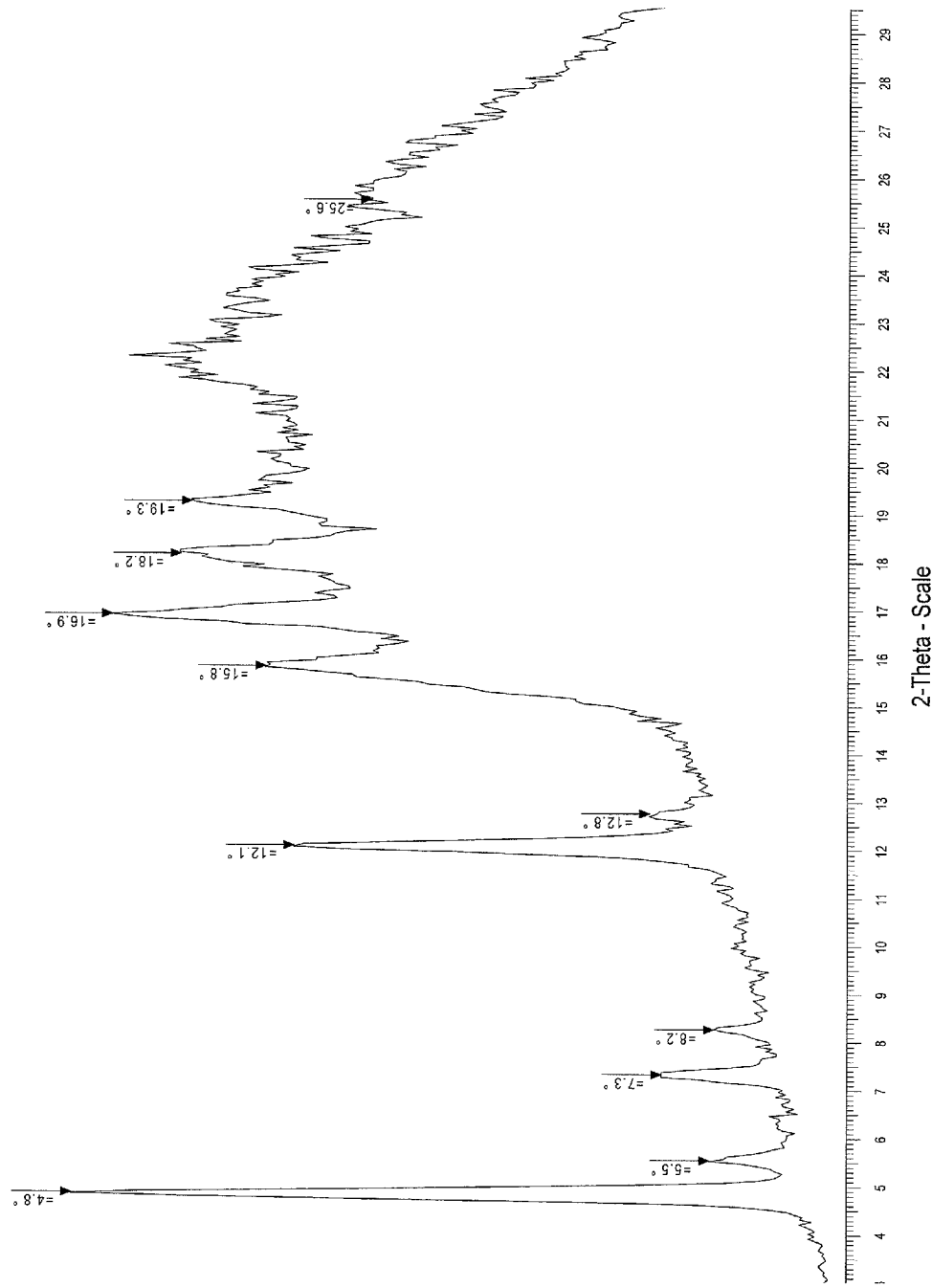
FIGURE: 5 COMPOUND 7

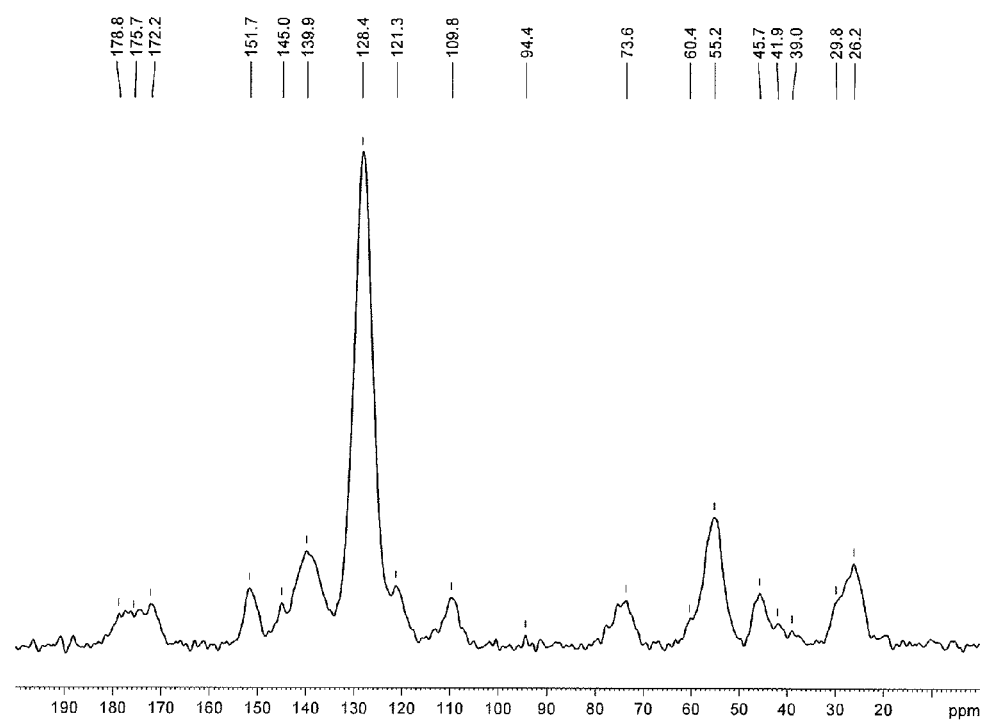
FIGURE: 6 COMPOUND 2

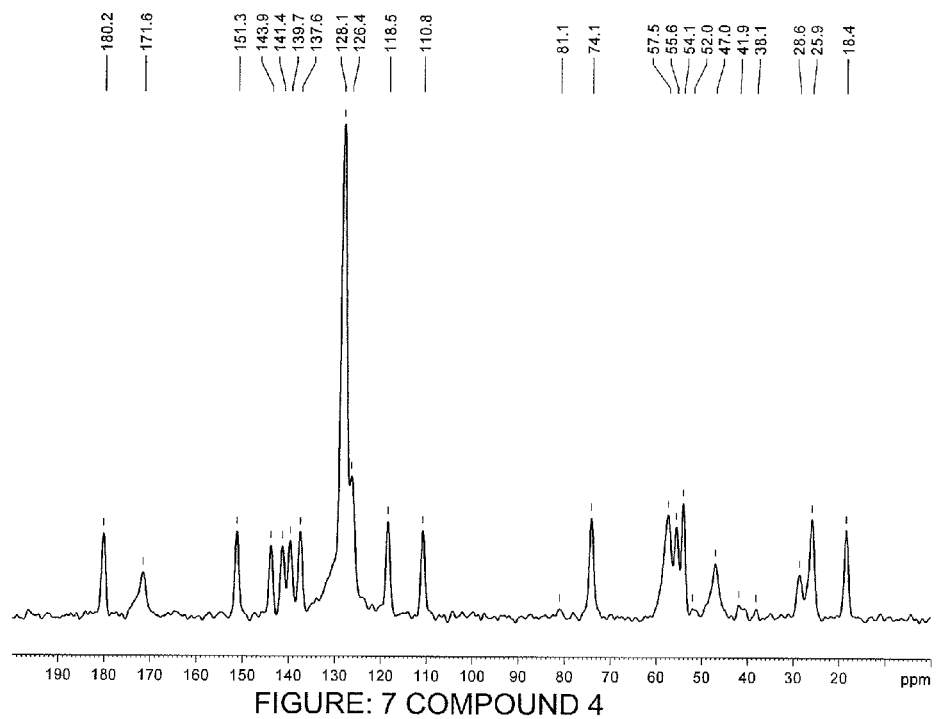
FIGURE: 7 COMPOUND 4
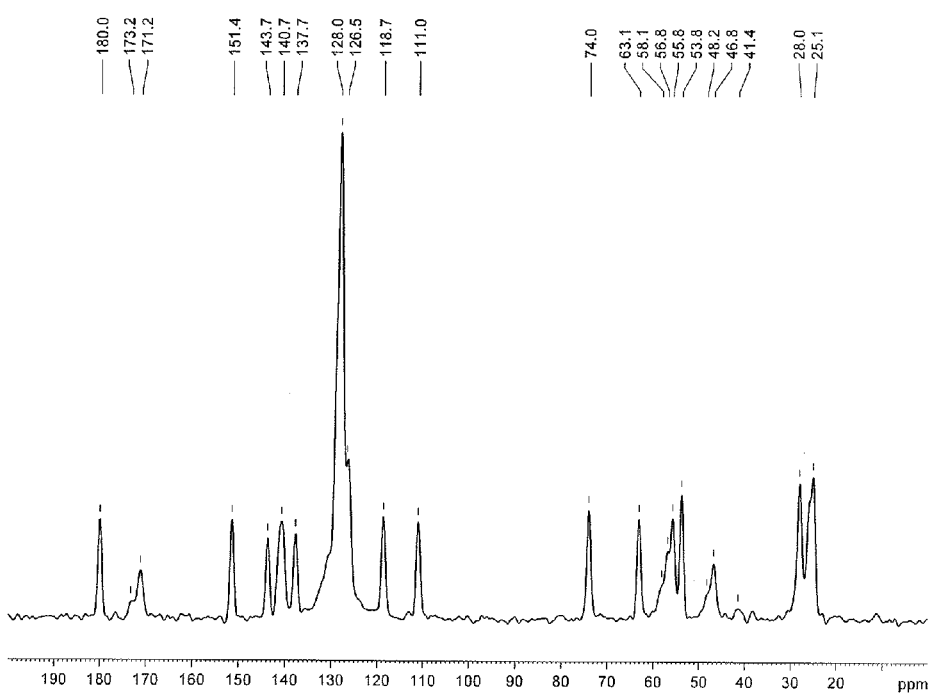
FIGURE: 8 COMPOUND 5

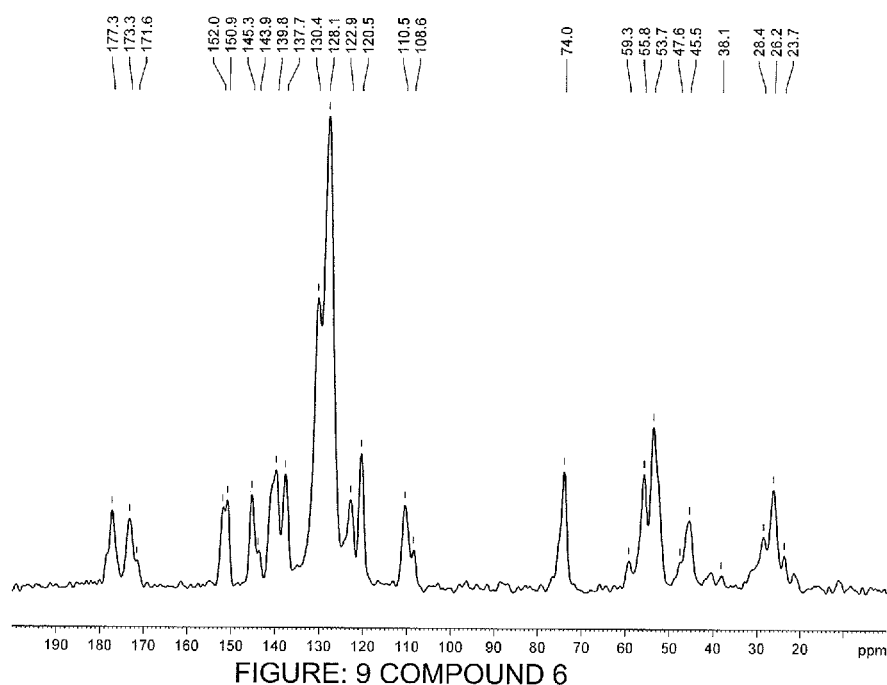
FIGURE: 9 COMPOUND 6
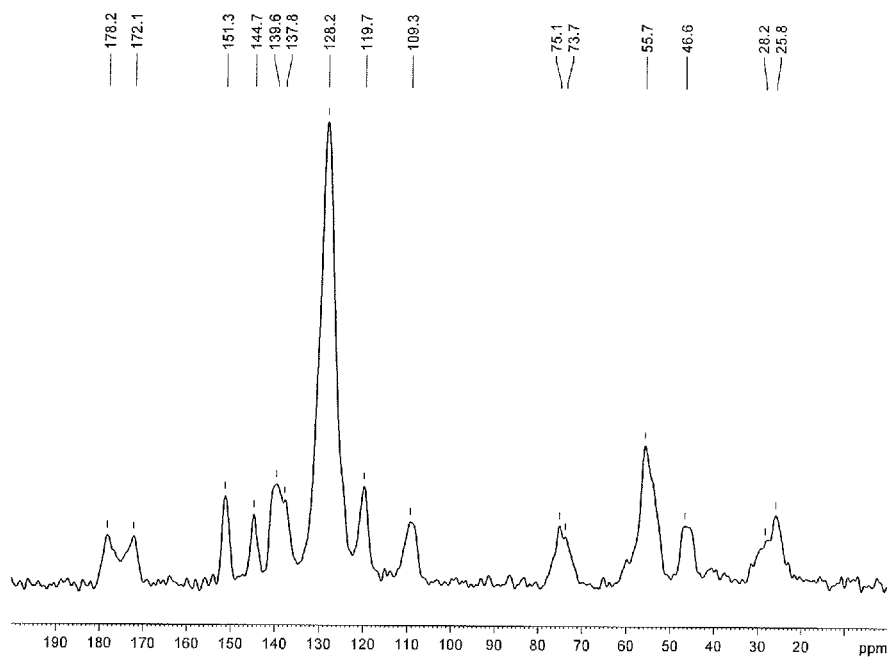
FIGURE 10: COMPOUND 7

Figure: 11
Mean Plasma Concentration of Compound 1 Time Curves Following Administration of Compounds 1, 2, 6, and 7 in Dogs
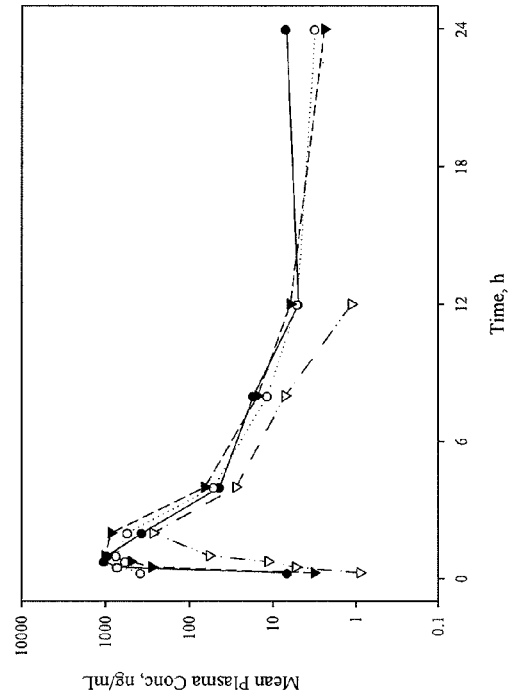
FIGURE: 11B
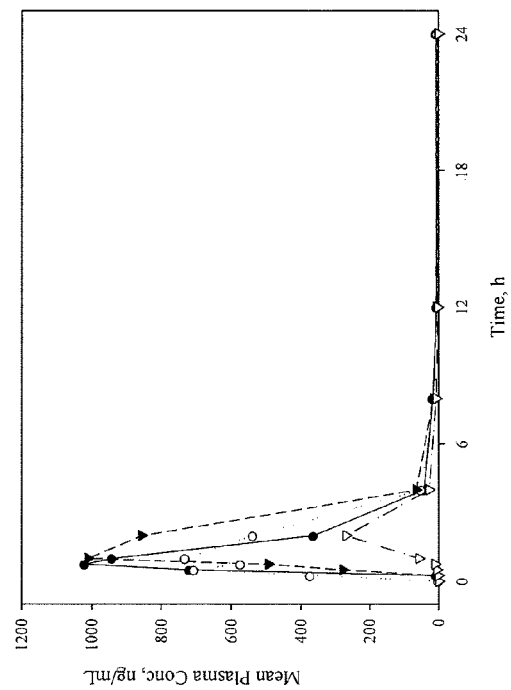
FIGURE: 11A

Figure: 12
Compound 1 Free Acid Mean Cmax and AUC(0-inf) Following Administration of Compounds 1, 2, 6, and 7 in Dogs
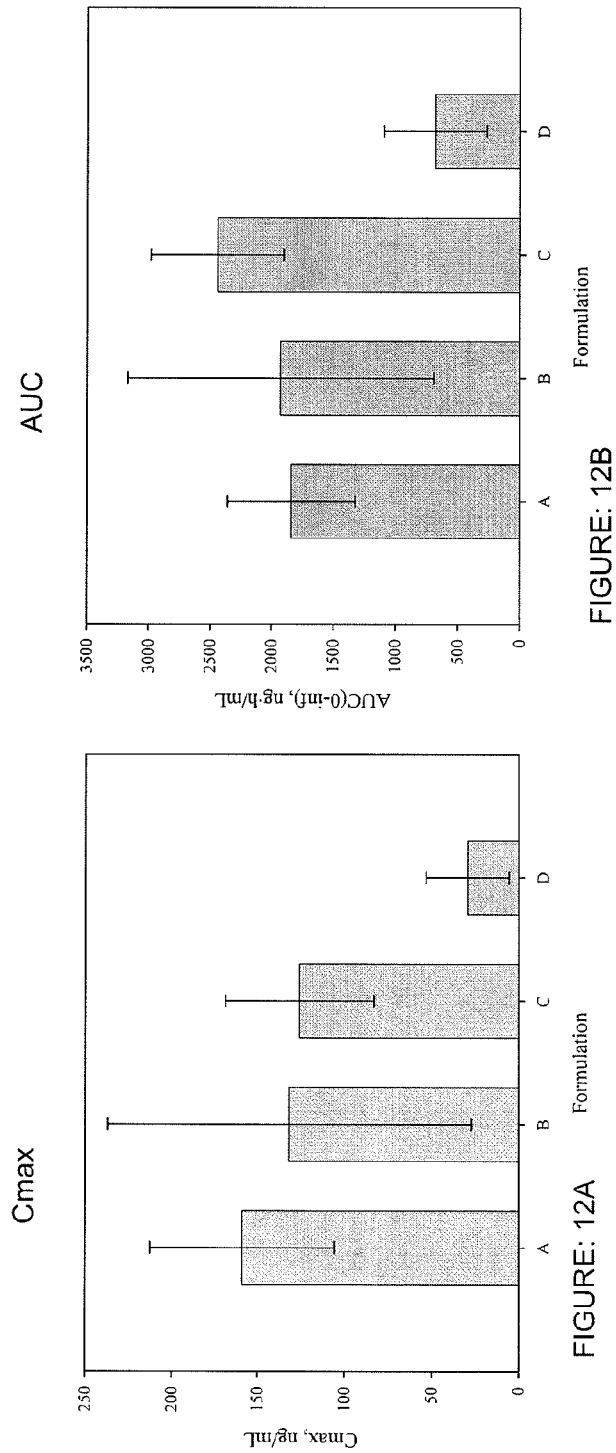
FIGURE: 12A
FIGURE: 12B
(A) Compound 2 Sodium Salt Amorphous
(B) Compound 6
(C) Compound 7
(D) Compound 1 Free Carboxylic Acid

SALTS AND SOLVATES OF A TETRAHYDROISOQUINOLINE DERIVATIVE

RELATED APPLICATIONS

This application is a divisional application of U.S. Ser. No. 13/187,882, filed on Jul. 21, 2011, now U.S. Pat. No. 8,614,227 which claims the benefit of U.S. Provisional Application Ser. No. 61/366,367, filed Jul. 21, 2010, which are hereby incorporated by reference in their entirety.

FIELD OF THE INVENTION (S)-2-(Diphenylacetyl)-1,2,3,4-tetrahydro-6-methoxy-5-(phenylmethoxy)-3-isoquinoline carboxylic acid in substantially pure form is described together with its sodium salt and solvates. Methods for preparing the compound, its sodium salt and its solvates and pharmaceutical compositions comprising them are also described.

BACKGROUND OF THE INVENTION (S)-2-(Diphenylacetyl)-1,2,3,4-tetrahydro-6-methoxy-5-(phenylmethoxy)-3-isoquinoline carboxylic acid, which is one enantiomer of the racemate known as PD 126055, is an angiotensin II type 2 ($AT_2$) receptor antagonist and is described in U.S. Pat. No. 5,246,943 and in Klutchko et al., 1994, Bioorg. & Med. Chem. Lett., 4:57-62.

$AT_2$ receptor antagonists have recently been identified as useful in treating pain, particularly inflammatory pain (WO 2007/106938) and neuropathic pain (WO 2006/066361) and (S)-2-(diphenylacetyl)-1,2,3,4-tetrahydro-6-methoxy-5-(phenylmethoxy)-3-isoquinoline carboxylic acid:

Compound 1

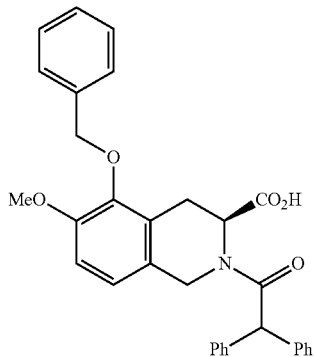

has been identified as a drug candidate.

Compound 1 has been obtained from the racemate by recrystallization of the α-methylbenzylamine salt (U.S. Pat. No. 5,246,943). However, this method does not provide adequate quantities of Compound 1 with required high levels of chemical and enantiomeric purity necessary for pharmaceutical purposes.

Although the racemate, ie: (R,S)-2-(diphenylacetyl)-1,2,3,4-tetrahydro-6-methoxy-5-phenylmethoxy)-3-isoquinoline carboxylic acid, is a crystalline compound and two different crystalline forms have been identified by the inventors, Compound 1 is an amorphous compound and despite significant effort, no crystalline form of the compound has been identified. There are significant difficulties in developing Compound 1 for pharmaceutical purposes including:

1. the amorphous form is difficult to purify to levels required for pharmaceutical purposes without resorting to expensive and time consuming chromatography methods;
2. the amorphous form of Compound 1 retains residual solvents which are difficult to remove to acceptable levels for pharmaceutical use; and
3. the amorphous form of Compound 1 has very low aqueous solubility and this limits its oral bioavailability.

There is a need for a form of Compound 1 that is suitable for pharmaceutical development, including a form that can be obtained in large quantities with acceptable chemical purity and enantiomeric purity and that has acceptable aqueous solubility.

The present invention is predicated, at least in part, by the discovery that the sodium salt of Compound 1 had a propensity to form highly crystalline solvates that not only allow this material to be manufactured with improved chemical purity but also allows the enantiomeric purity to be improved by recrystallization in the event that some epimerization occurs at the chiral 3-position of the tetrahydroisoquinoline ring during the manufacturing process. The sodium salt was also found to have good oral bioavailability characteristics.

SUMMARY OF THE INVENTION

In a first aspect there is provided the sodium salt of (S)-2-(diphenylacetyl)-1,2,3,4-tetrahydro-6-methoxy-5-(phenylmethoxy)-3-isoquinoline carboxylic acid and solvates thereof.

In a particular embodiment, the sodium salt is in an amorphous form. In other embodiments, the sodium salt is in the form of a crystalline solvate, especially an ethanolate, isopropanolate or hydrate. In some embodiments, the hydrate is a monohydrate, dihydrate, trihydrate, tetrahydrate, or a full or fractional hydrate in between one and five. In some embodiments, the hydrate has about 2 to about 5 molecules of water.

In another aspect there is provided (S)-2-(diphenylacetyl)-1,2,3,4-tetrahydro-6-methoxy-5-(phenylmethoxy)-3-isoquinoline carboxylic acid in substantially pure form.

In a particular embodiment, the compound has an enantiomeric purity of >97% ee and/or >96% chemical purity.

In another aspect of the invention there is provided a pharmaceutical composition comprising the (S)-2-(diphenylacetyl)-1,2,3,4-tetrahydro-6-methoxy-5-(phenylmethoxy)-3-isoquinoline carboxylic acid, its sodium salt or a solvate of the sodium salt together with a pharmaceutically acceptable carrier, diluent or excipient.

In some embodiments, the composition comprises the sodium salt. In some embodiments, the composition is in a solid form, especially for oral delivery. In some embodiments, the sodium salt is in an amorphous form.

In yet another aspect of the invention, there is provided a method of preparing the sodium salt of (S)-2-(diphenylacetyl)-1,2,3,4-tetrahydro-6-methoxy-5-(phenylmethoxy)-3-isoquinoline carboxylic acid comprising:
 (i) treating (S)-2-(diphenylacetyl)-1,2,3,4-tetrahydro-6-methoxy-5-(phenylmethoxy)-3-isoquinoline carboxylic acid with sodium alkoxide;
 (ii) forming a crystalline alcohol solvate of the resulting sodium salt of (S)-2-(diphenylacetyl)-1,2,3,4-tetrahydro-6-methoxy-5-(phenylmethoxy)-3-isoquinoline carboxylic acid; and
 (iii) recrystallizing the solvate formed in step (ii).

In one embodiment, the sodium alkoxide is sodium ethoxide. In a particular embodiment the crystalline solvate is the ethanol or iso-propanol solvate, especially the iso-propanol solvate.

In some embodiments, the solvate molecule of the crystalline alcohol solvate formed in step (ii) is exchanged for another solvate molecule before, during or after step (iii). In a particular embodiment, the crystalline alcohol solvate obtained in step (ii) is an ethanol solvate and recrystallization in step (iii) is achieved in a solvent comprising iso-propanol such that the crystalline solvate obtained in step (iii) is the iso-propanol solvate of the sodium salt of Compound 1. In some embodiments, the recrystallization of step (iii) is performed in a non-aqueous organic solvent.

The method may further comprise the step of exchanging the alcohol within the solvate for water molecules to prepare amorphous or crystalline hydrates of the sodium salt.

The method may further comprise the step of drying the alcohol solvate or hydrate to provide the amorphous sodium salt of (S)-2-(diphenylacetyl)-1,2,3,4-tetrahydro-6-methoxy-5-(phenylmethoxy)-3-isoquinoline carboxylic acid. In some embodiments, drying is by lyophilization.

The method may further comprise the step of acidifying the sodium salt to provide (S)-2-(diphenylacetyl)-1,2,3,4-tetrahydro-6-methoxy-5-(phenylmethoxy)-3-isoquinoline carboxylic acid in substantially pure form.

In yet a further aspect, there is provided a method of preparing an alcohol solvate of the sodium salt of (S)-2-(diphenylacetyl)-1,2,3,4-tetrahydro-6-methoxy-5-(phenylmethoxy)-3-isoquinoline carboxylic acid comprising the steps of:
(i) acylating the isoquinoline nitrogen atom of (S)-1,2,3,4-tetrahydro-6-methoxy-5-(phenylmethoxy)-3-isoquinoline carboxylic acid with an activated cyclic amide of the formula:

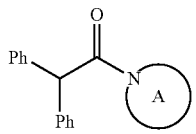

wherein ring A is a 5 membered nitrogen-containing heterocycle; and
(ii) treating the product of step (i) with an alkoxide salt in an alcohol solvent.

In some embodiments, the 5 membered nitrogen-containing heterocycle is pyrazole, pyrrole, imidazole, 1,2,3-trazole or 1,2,4-triazole, especially pyrazole. In some embodiments the alkoxide salt is sodium ethoxide. In some embodiments the alcohol solvent is ethanol.

All publications and patent applications mentioned in this specification are incorporated by reference in their entirety to the same extent as if each individual publication or patent application was specifically and individually indicated to be incorporated by reference.

BRIEF DESCRIPTION OF THE DRAWINGS

FIG. 1 illustrates the characteristic X-ray powder diffraction pattern of a crystalline sodium salt of Compound 2.

FIG. 2 illustrates the characteristic X-ray powder diffraction pattern of a crystalline ethanol solvate of the sodium salt (Compound 4).

FIG. 3 illustrates the characteristic X-ray powder diffraction pattern of a crystalline iso-propanol solvate of the sodium salt (Compound 5).

FIG. 4 illustrates the characteristic X-ray powder diffraction pattern of a crystalline hydrate of the sodium salt that has at least three water molecules (Compound 6).

FIG. 5 illustrates the characteristic X-ray powder diffraction pattern of a crystalline hydrate of the sodium salt that has about two water molecules (Compound 7).

FIG. 6 illustrates a characteristic solid state $^{13}C$ NMR spectrum of an amorphous sodium salt of Compound 2.

FIG. 7 illustrates a characteristic solid state $^{13}C$ NMR spectrum of a crystalline ethanol solvate of the sodium salt (Compound 4).

FIG. 8 illustrates a characteristic solid state $^{13}C$ NMR spectrum of a crystalline iso-propanol solvate of the sodium salt (Compound 5).

FIG. 9 illustrates a characteristic solid state $^{13}C$ NMR spectrum of a crystalline hydrate of the sodium salt that has at least three water molecules (Compound 6).

FIG. 10 illustrates a characteristic solid state $^{13}C$ NMR spectrum of a crystalline hydrate of the sodium salt that has about two water molecules (Compound 7).

FIG. 11 depicts the mean plasma concentration of (S)-2-(diphenylacetyl)-1,2,3,4-tetrahydro-6-methoxy-5-(phenylmethoxy)-3-isoquinoline carboxylic acid (compound 1) over time following oral administration of Compounds 1, 2 (amorphous sodium salt), 6, and 7 to dogs. FIG. 11A depicts the mean plasma concentration time curves on a linear scale and FIG. 11B depicts the mean plasma concentration time curves on a log scale.

FIG. 12A provides the Cmax of the free acid Compound 1 following oral administration of Compounds 1, 2 (amorphous sodium salt), 6, and 7 to dogs. FIG. 12B provides the AUC (0-inf) of the free acid Compound 1 following oral administration of Compounds 1, 2 (amorphous sodium salt), 6, and 7 to dogs.

DETAILED DESCRIPTION OF THE INVENTION

The sodium salt of (S)-2-(diphenylacetyl)-1,2,3,4-tetrahydro-6-methoxy-5-(phenylmethoxy)-3-isoquinoline carboxylic acid (hereinafter referred to as Compound 2) has the formula:

Compound 2

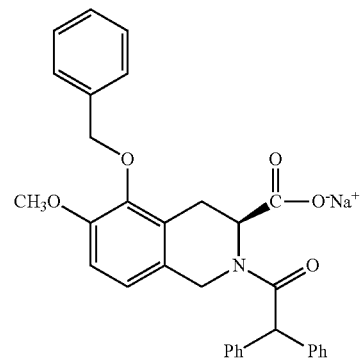

This compound is an $AT_2$ receptor antagonist with pharmaceutical uses in treating pain, especially inflammatory and neuropathic pain. Compound 1 and its racemic mixture have been previously identified as an $AT_2$ receptor antagonist. However, the sodium salt (Compound 2) has now been found to have particular advantages in relation to ease of manufacture, purity and oral bioavailability not found in the free acid (Compound 1) or other salts.

While the racemic form is crystalline, the single enantiomer represented by Compound 1 has not been isolated in a crystalline form and therefore purification to pharmaceutically acceptable levels is difficult, including removal of its (R)-enantiomer (Compound 3):

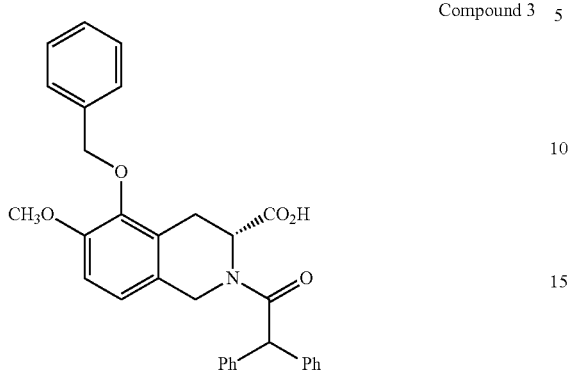

Compound 3

Furthermore, epimerization at the chiral 3-position of Compound 1 can occur under some manufacturing conditions and therefore obtaining and maintaining Compound 1 with a high enantiomeric purity can be a challenge.

The present inventors have found that the sodium salt, Compound 2, can be isolated in crystalline form as a solvate, particularly an alcohol solvate. This may be achieved directly from the preparation of Compound 1 and therefore purification by crystallization is possible and high enantiomeric purity may be achieved. Furthermore, if epimerization of the chiral centre at the 3-position occurs, crystallization can be used to remove the unwanted enantiomer and to improve enantiomeric purity. The solvates may also be exchanged with one another and conversion to hydrate forms with pharmaceutically acceptable purity and residual solvent levels can be achieved. These hydrate forms include crystalline forms as well as an amorphous form, with the latter being prepared by lyophilization.

In a particular embodiment, Compound 2 is in amorphous form. In one such embodiment, the amorphous form exhibits a solid state $^{13}$C NMR spectrum comprising peaks at about 55.2, 109.8, 128.4 and 151.7 ppm. In another such embodiment, the amorphous form exhibits a solid state $^{13}$C NMR spectrum substantially the same as FIG. 6. In another embodiment, the solid state $^{13}$C NMR spectrum has peaks at about 26.2, 29.8, 39.0, 41.9, 45.7, 55.2, 60.4, 73.6, 94.4, 109.8, 121.3, 128.4, 139.9, 145.0, 151.7, 172.2, 175.7 and 178.8 ppm.

In another embodiment, Compound 2 is in a crystalline form. In one such embodiment, the non-solvated sodium salt crystalline form exhibits an XRPD pattern comprising at least one peak at about 9.6 degrees 2θ. In another such embodiment, the crystalline form exhibits an XRPD pattern comprising a peak at about 9.6 degrees 2θ and comprising at least one peak selected from the group consisting of about 6.0 and 19.6 degrees 2θ. In another such embodiment, the crystalline form exhibits an XRPD pattern comprising a peak at about 9.6 degrees 2θ, at least one peak selected from the grouping consisting of about 6.0, and 19.6 degrees 2θ, and at least one peak selected from the group consisting of about 14.0, 17.9, 20.6, 21.8, 23.3, and 23.9 degrees 2θ. In another such embodiment, the crystalline form exhibits an XRPD pattern substantially the same as FIG. 1. In another such embodiment, the non-solvated crystalline form has an X-ray diffraction pattern with peaks at 2θ=5.5, 6.0, 6.9, 8.5, 9.6, 11.0, 13.3, 14.0, 16.1, 16.7, 17.9, 18.4, 19.6, 20.6, 21.8, 22.3, 23.3, 23.9, 25.5, 26.3 and 27.6.

In some embodiments, the solvate is formed from water or an alcoholic solvent, especially water, ethanol or iso-propanol.

In one embodiment, the solvate of the sodium salt is the ethanol solvate (ethanolate) (Compound 4):

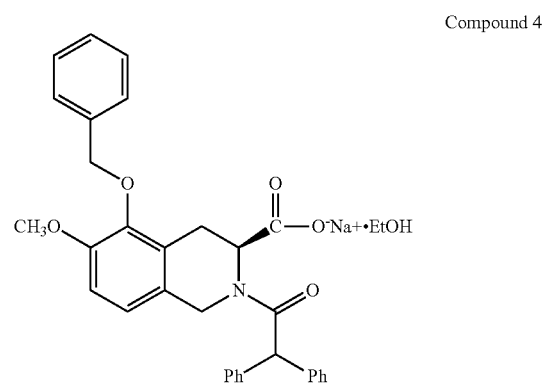

Compound 4

In one embodiment, this compound can be isolated in a crystalline form. In one such embodiment the ethanol solvate exhibits an X-ray powder diffraction ("XRPD") pattern comprising a peak at about 14.3 degrees 2θ. In another such embodiment, the ethanol solvate sodium salt crystalline form exhibits XRPD pattern comprising a peak at about 14.7 degrees 2θ. In another such embodiment, the ethanol solvate sodium salt crystalline form exhibits XRPD pattern comprising a peak at least two of the group comprising about 14.3, 14.7, 26.9, and 29.7 degrees 2θ. In another such embodiment, the crystalline form exhibits an XRPD pattern substantially the same as FIG. 2. In another such embodiment, the crystalline form has an X-ray diffraction pattern with peaks at 2θ=5.5, 6.7, 8.0, 8.7, 9.3, 11.1, 13.4, 14.3, 14.7, 15.8, 16.1, 16.6, 17.4, 17.8, 18.8, 20.3, 20.9, 21.4, 22.2, 22.8, 24.2, 25.4, 26.9, 27.6, 28.7, 29.7, 30.3, 31.3, 32.1, 33.5, 35.7 and 41.0.

In one embodiment, the ethanol solvate of the sodium salt crystalline form exhibits a solid state $^{13}$C NMR spectrum comprising peaks at about 18.4, about 139.7, and about 141.4 ppm. In another such embodiment the ethanol solvate of the sodium salt crystalline form exhibits a solid state $^{13}$C NMR spectrum substantially the same as FIG. 7. In another embodiment, the solid state $^{13}$C NMR spectrum has peaks at about 18.4, 25.9, 28.6, 38.1, 41.9, 47.0, 52.0, 54.1, 55.6, 57.5, 74.1, 81.1, 110.8, 118.5, 126.4, 128.1, 137.6, 139.7, 141.4, 143.9, 151.3, 171.6 and 180.2 ppm.

In another embodiment, the solvate of the sodium salt is the iso-propanol solvate (iso-propanolate) (Compound 5):

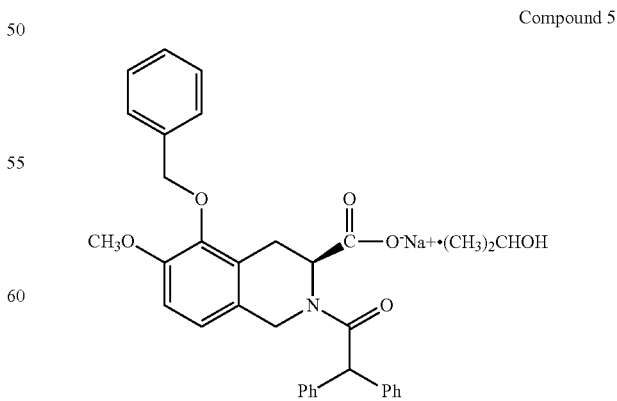

Compound 5

This compound can be isolated in a crystalline form. In one such embodiment, the iso-propanol solvate of the sodium salt crystalline form exhibits an XRPD pattern comprising at least one peak selected from the group consisting of about 26.0, 26.6, 27.2, 28.3, and 29.3 degrees 2θ. In another such embodiment, the crystalline form exhibits an XRPD pattern comprising at least two peaks selected from the group consisting of about 25.0, 26.0, 26.6, 27.2, 28.3, and 29.3 degrees 2θ. In another such embodiment, the crystalline form exhibits an XRPD pattern comprising at least one peak selected from the grouping consisting of about 26.0, 26.6, 27.2, 28.3, and 29.3 degrees 2θ, and at least one peak selected from the group consisting of about 10.8, 14.0, 21.1, 21.9, and 22.5 degrees 2θ. In another such embodiment, the crystalline form exhibits an XRPD pattern substantially the same as FIG. 3. In another embodiment, this iso-propanol solvate crystalline form has an X-ray diffraction pattern with peaks at 2θ=5.4, 6.6, 7.9, 8.6, 9.2, 10.8, 13.4, 14.0, 15.9, 16.4, 17.3, 17.6, 18.6, 20.0, 20.5, 21.1, 21.9, 22.5, 23.0, 24.0, 25.0, 25.5, 26.0, 26.6, 27.2, 28.3 and 29.3.

In one embodiment, the iso-propanol solvate of the sodium salt crystalline form exhibits a solid state $^{13}$C NMR spectrum comprising peaks at about 63.1, and about 140.7 ppm. In another such embodiment the iso-propanol solvate of the sodium salt crystalline form exhibits a solid state $^{13}$C NMR spectrum substantially the same as FIG. 8. In another embodiment, the solid state $^{13}$C NMR spectrum has peaks at about 25.1, 28.0, 41.4, 46.8, 48.2, 53.8, 55.8, 56.8, 58.1, 63.1, 74.0, 111.0, 118.7, 126.5, 128.0, 137.7, 140.7, 143.7, 151.4, 171.2, 173.2 and 180.0 ppm.

In another embodiment, the solvate of the sodium salt is the trihydrate solvate (Compound 6) containing three molecules of water for every molecule of Compound 2.

Compound 6

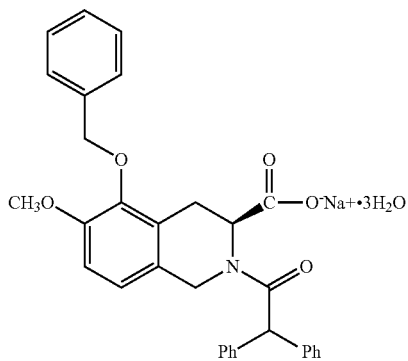

Some studies indicate that Compound 6 may have four or more molecules (a fractional hydrate) of water for every molecule of Compound 2. Regardless of the exact amount of water, the hydrate of Compound 6 can be isolated in crystalline form. In one such embodiment, the hydrate of the sodium salt crystalline form having between three and 5 water molecules exhibits an XRPD pattern comprising a peak at about 15.2 degrees 2θ. In another such embodiment, the crystalline form exhibits an XRPD pattern comprising a peak at about 15.2 degrees, and at least two peaks selected from the group consisting of about 4.8, 7.3, 12.0, 12.6, 23.5, and 24.5 degrees 2θ. In another such embodiment, the crystalline form exhibits an XRPD pattern substantially the same as FIG. 4. In another embodiment, this hydrate crystalline form has an X-ray diffraction pattern with peaks at 2θ=4.8, 5.5, 7.3, 8.3, 9.9, 12.0, 12.6, 15.2, 16.7, 17.2, 17.9, 19.0, 21.5, 23.5 and 24.5.

In one embodiment, the hydrate of the sodium salt crystalline form having about 3 to less than 5 water molecules exhibits a solid state $^{13}$C NMR spectrum comprising peaks at about 53.7, about 122.9, and about 128.1 ppm. In another such embodiment the hydrate of the sodium salt crystalline form having about 3 to less than 5 water molecules exhibits a solid state $^{13}$C NMR spectrum substantially the same as FIG. 9. In another embodiment, the solid state $^{13}$C NMR spectrum has peaks at about 23.7, 26.2, 28.4, 38.1, 45.5, 47.6, 53.7, 55.8, 59.3, 74.0, 108.6, 110.5, 120.5, 122.9, 128.1, 130.4, 137.7, 139.8, 143.9, 145.3, 150.9, 152.0, 171.6, 173.3 and 177.3 ppm In yet another embodiment, the solvate of the sodium salt is the dihydrate solvate (Compound 7) containing two molecules of water for every molecule of Compound 2.

Compound 7

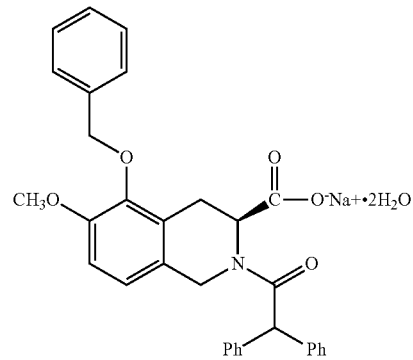

Some studies indicate that Compound 7 may have slightly less than two, but more than one molecule of water (a fractional hydrate) for every molecule of Compound 2. Regardless of the exact amount of water, the hydrate of Compound 7 can be isolated in crystalline form. In one such embodiment, the hydrate of the sodium salt crystalline form having 1-2 water molecules exhibits an XRPD pattern comprising at least one peak at about 19.3 degrees 2θ. In another such embodiment, the crystalline form exhibits an XRPD pattern comprising peaks at about 19.3 and 18.2 degrees 2θ. In another such embodiment, the crystalline form exhibits an XRPD pattern substantially the same as FIG. 5. In another embodiment, this hydrate crystalline form has an X-ray diffraction pattern with peaks at 2θ=4.8, 5.5, 7.3, 8.2, 12.1, 12.8, 15.8, 16.9, 18.2, 19.3 and 25.6.

In one embodiment, the hydrate of the sodium salt crystalline form having about 1-2 water molecules exhibits a solid state $^{13}$C NMR spectrum comprising peaks at about 55.7, about 128.2, and about 151.3 ppm. In another such embodiment the hydrate of the sodium salt crystalline form having about 1-2 water molecules exhibits a solid state $^{13}$C NMR spectrum substantially the same as FIG. 10. In another embodiment, the solid state $^{13}$C NMR has peaks at about 25.8, 28.2, 46.6, 55.7, 73.7, 75.1, 109.3, 119.7, 128.2, 137.8, 139.6, 144.7, 151.3, 172.1 and 178.2 ppm.

As used herein, the term "enantiomeric purity" refers to the percentage of (S)-enantiomer present compared to the unwanted (R)-enantiomer. For example a purity of 90% has 90% (S)-enantiomer and 10% (R)-enantiomer and a purity of 100% has only (S)-enantiomer and no (R)-enantiomer. In particular embodiments, the purity of the (S)-enantiomer is high, that is above 80%, especially above 85%, 87.5%, 90%, 92.5%, 95%, 96%, 97%, 98%, 99% and includes 100%. Enantiomeric purity may also be reported as enantiomeric excess (ee). Enantiomeric excess is usually expressed as a percentage calculated by the following equation:

$$((R-S)/(R+S))\times 100 = \% \text{ ee}$$

where R and S are the respective fractions of the enantiomers such that R+S=1. In particular embodiments, the ee of the (S)-enantiomer is high, that is above 80%, especially above 85%, 87.5%, 90%, 92.5%, 95%, 96%, 97%, 98%, 99% and includes 100%.

As used herein, the term "chemical purity" refers to the percentage of impurities present in the product. Impurities may be in the form of, for example, the presence of unwanted solvents, degradation products or oxidation products. In particular embodiments the chemical purity is high, that is above 80% of the product is (S)-2-(diphenylacetyl)-1,2,3,4-tetrahydro-6-methoxy-5-(phenylmethoxy)-3-isoquinoline carboxylic acid, especially above 85%, 87.5%, 90%, 92.5%, 95%, 96%, 97%, 98%, 99% and includes 100%.

The term "substantially pure form" refers to a product having greater than 96% chemical purity, especially greater than 97%, 98% or 99% and more especially 100% chemical purity and/or greater than 97% ee, especially greater than 98% or 99% ee and more especially 100% ee.

As used herein, the meaning of the term "about" depends upon the context in which it is used. When used with respect to the position of a peak on an x-ray powder diffraction (XRPD) pattern, the term "about" includes peaks within ±0.1 degrees 2θ of the stated position. For example, as used herein, an XRPD peak at "about 10.0 degrees 2θ" means that the stated peak occurs from 9.9 to 10.1 degrees 2θ. When used with respect to the position of a peak on a solid state $^{13}$C NMR spectrum, the term "about" includes peaks within ±0.2 ppm of the stated position. For example, as used herein, a $^{13}$C NMR spectrum peak at "about 100.0 ppm" means that the stated peak occurs from 99.8 to 100.2 ppm.

Synthetic methods for the preparation of Compound 1 are known in the art. The synthesis of the racemic mixture containing Compound 1 and its (R)-enantiomer Compound 3, followed by resolution of the enantiomers using chiral salt formation is described in U.S. Pat. No. 5,246,943 and Klutchko et al., Bioorg. & Med. Chem. Lett., 1994, 4:57-62. The chiral salt used for resolution was 1-(−)-α-methylbenzylamine.

The sodium salt, Compound 2, can be obtained by treating Compound 1 with an aqueous solution of sodium hydroxide. However, this method prepares Compound 2 as an oily residue or gum rather than a crystalline solid. Crystalline forms of the sodium salt are not obtained unless solvent systems are chosen that lead to the formation of crystalline solids in the form of different solvates. For example, the ethanol solvate, Compound 4, can be obtained by taking the non-crystalline form of Compound 2 prepared using an aqueous solution of sodium hydroxide and treating it with ethanol or more preferably by treating Compound 1 with sodium ethoxide in ethanol. Similarly, the iso-propanol solvate, Compound 5, can be prepared by taking the non-crystalline form of Compound 2 prepared using an aqueous solution of sodium hydroxide and treating it with iso-propanol. Compound 5 could also be prepared by treating Compound 1 with sodium iso-propoxide in iso-propanol containing solvent systems.

Compound 2 or its solvates may also be obtained by recrystallizing an alcohol solvate of Compound 2 in an organic solvent or an aqueous organic solvent (organic solvent with added percentage of water). Crystalline solvates were obtained by recrystallization in ethyl acetate (EtOAc)/10% water, methylethylketone (MEK), 1-propanol, EtOAc, tert-butylmethyl ether (TBME) and hydrocarbon solvents such as heptane. Recrystallization from acetonitrile gave a non-solvated crystalline form of the sodium salt.

The hydrates, Compounds 6 and 7, can be obtained by exposure of the crystalline ethanolate or iso-propanolate to moisture, especially atmospheric moisture. At high humidity such as 70% relative humidity, the Compound 6 hydrate is formed, in moderate humidity such as 40% relative humidity, the Compound 7 hydrate is formed. Upon drying or lyophilization of the different hydrate forms, the amorphous sodium salt (Compound 2) is produced.

The amorphous form of Compound 2 can also be formed by lyophilization of an alcohol solvate of Compound 2 in water.

Alternatively, Compound 2 can be prepared by asymmetric synthesis and the sodium salt isolated as a crystalline solvate at the end of the synthesis. There are methods known in the art for preparing non-natural chiral α-amino acids (for example, Burk et al., J. Am. Chem. Soc., 1993, 115, 10125-10138) and such methods can be applied to the synthesis of a chiral ortho-phenylmethyloxy-meta-methoxy-phenylalanine. Care must be taken to use conditions that are sufficiently mild as to allow the retention of the pendent O-benzyl group.

Once prepared, the chiral phenylalanine derivative can be transformed into a 1,2,3,4-tetrahydroisoquinoline using the Pictet-Spengler reaction as shown in Scheme 1 and described in U.S. Pat. No. 5,246,943.

Scheme 1

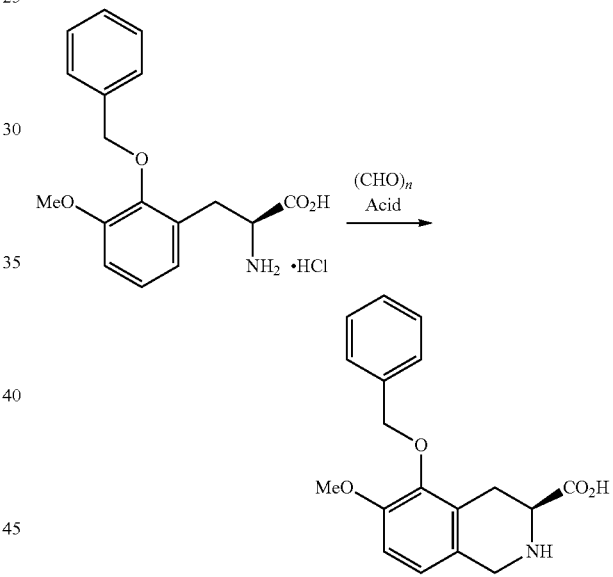

Acylation of the isoquinoline nitrogen atom may be achieved by reaction of the isoquinoline with 2,2-diphenylethanoic acid which has been activated for reaction to form an amide bond, for example, 2,2-diphenylethanoic acid chloride, anhydride or a cyclic active amide. This reaction must be carefully controlled as yields can be decreased by the formation of dimeric, esterified or epimerized byproducts. Side reactions can be avoided or reduced by using anhydrous conditions and protecting the carboxylic acid during acylation of the isoquinoline nitrogen with an acid chloride. For example, during the formation of the amide bond using 2,2-diphenylethanoic acid chloride, an easily hydrolyzed protecting group, such as a trimethylsilyl group, that is hydrolyzed during aqueous work up, may be used to prevent or reduce side reactions at the carboxylic acid. Suitable protecting groups are known in the art and may be found in Greene and Wuts, Protective Groups in Organic Synthesis, 3$^{rd}$ Edition, 1999, John Wiley & Sons.

Use of a cyclic active amide of 2,2-diphenylethanoic acid reduces the need for this temporary protection of the isoquinoline carboxylic acid as the cyclic active amide is more selective for reaction with the isoquinoline nitrogen. The cyclic active amide may be formed by reaction of the 2,2-diphenyl ethanoic acid chloride with a 5 membered nitrogen containing heterocycle. Examples of suitable heterocycles include pyrazole, pyrrole, imidazole, 1,2,3-triazole and 1,2,4-triazole. An example using pyrazole is shown in Scheme 2.

The knowledge of different solvates and physical forms of Compound 2 is incorporated into the overall synthetic process by preparing the ethanol solvate of the sodium salt, Compound 4, for example, by adding sodium ethoxide in ethanol to the organic extract following aqueous work up of the acylation reaction and isolating the crystalline intermediate directly from the reaction mixture as shown in Scheme 2.

Scheme 2

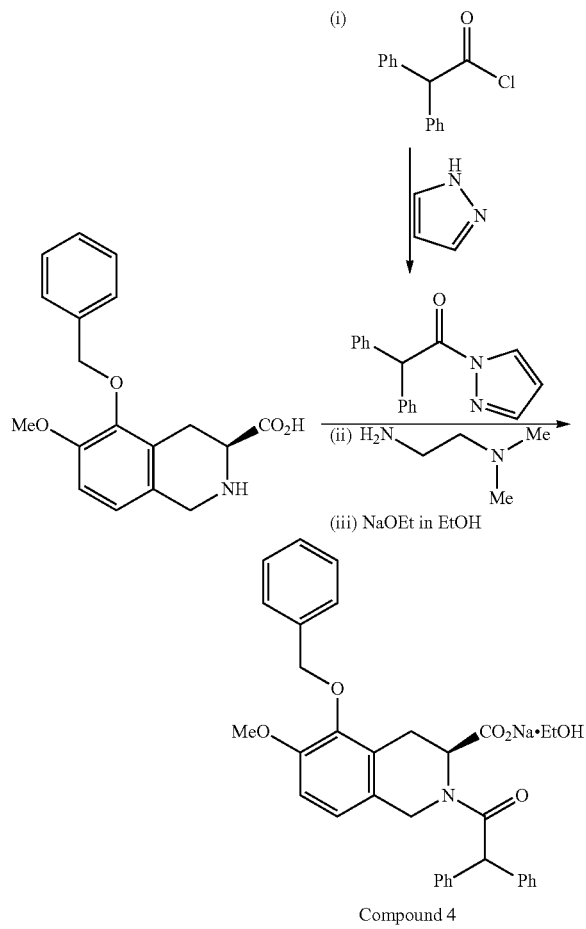

Compound 4

Accordingly, in a further aspect of the invention there is provided a method of preparing an alcohol solvate of the sodium salt of (S)-2-(diphenylacetyl)-1,2,3,4-tetrahydro-6-methoxy-5-(phenylmethoxy)-3-isoquinoline carboxylic acid comprising the steps of:
(i) acylating the isoquinoline nitrogen atom of (S)-1,2,3,4-tetrahydro-6-methoxy-5-(phenylmethoxy)-3-isoquinoline carboxylic acid with an activated cyclic amide of the formula:

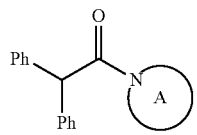

wherein ring A is a 5 membered nitrogen-containing heterocycle; and
(ii) treating the product of step (i) with an alkoxide salt in an alcohol solvent.

In some embodiments, the 5 membered nitrogen-containing heterocycle is pyrazole, pyrrole, imidazole, 1,2,3-triazole or 1,2,4-triazole. In one embodiment, the 5 membered nitrogen containing heterocycle is pyrazole. In some embodiments the alkoxide salt is sodium ethoxide. In some embodiments the alcohol solvent is ethanol. In some embodiments the combination of sodium ethoxide and ethanol is used.

In some embodiments the product of step (i) is treated with base, such an amine base, before step (ii).

Compound 4 can be further purified by recrystallization in ethanol containing solvent systems to provide crystalline Compound 4. Likewise, if Compound 5 was prepared, it may be purified by recrystallization in an iso-propanol solvent system. The alcohol solvates can be converted by crystallization in a different alcohol containing solvent system. For example, Compound 5 may be made by recrystallization from iso-propanol or mixtures of iso-propanol and another polar solvent such as ethyl acetate, to give the iso-propanol solvate (Compound 5).

Compounds 4 or 5 may be stored, converted to the different crystalline forms of the hydrates of Compound 2 or dissolved in water and lyophilized to provide amorphous Compound 2.

The sodium salt, Compound 2, can be prepared in crystalline or amorphous forms suitable for use in a pharmaceutical composition, by treating the free acid (Compound 1), either during synthesis or after its isolation, with a sodium alkoxide, then forming a crystalline solvate.

As used herein, an "alkoxide" refers to an ion formed by removal of hydrogen atom from the hydroxyl group of an alcohol. Suitable alkoxides that may be used in the present invention include methoxide, ethoxide, propoxide, iso-propoxide and butoxide.

The crystalline solvate of Compound 2 may be formed by treatment with the sodium alkoxide by using a suitable solvent. For example, the ethanol solvate of Compound 2 may be formed by treatment with sodium ethoxide in ethanol. The iso-propanol solvate may be formed by treatment with sodium iso-propoxide in iso-propanol.

Once the crystalline solvate is isolated, it is recrystallized from a suitable solvent. Recrystallization of the isolated solvate may be performed or the solvate may be exchanged for another solvate before or during recrystallization. For example, the ethanol solvate may be isolated and then the ethanol molecule exchanged with an iso-propanol molecule to give the iso-propanol solvate which is recrystallized.

The recrystallized alcohol solvate may then be converted to hydrate forms through exposure to atmospheric moisture and/or dried or lyophilized to give amorphous Compound 2 in high chemical and enantiomeric purity. In some embodiments the crystalline alcohol solvate or hydrate is dissolved in water and lyophilized to give amorphous Compound 2 in high chemical and enantiomeric purity or substantially pure form.

The sodium salt (Compound 2) may also be acidified to give the free acid (Compound 1) in substantially pure form.

Although it is possible to use the compounds of the invention in neat form, it is more suitably used in a pharmaceutical composition together with at least one pharmaceutically acceptable carrier, diluent or excipient.

The carrier(s), diluent(s) or excipient(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The compounds of the invention, especially Compound 2, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, and such unit dosage forms may contain any suitable effective amount of the active ingredient commensurate with the intended daily dosage range to be employed. Formulations containing ten (10) milligrams or (25) milligrams of active ingredient or, more broadly, 0.1 to two hundred (200) milligrams, per tablet or capsule, are accordingly suitable representative unit dosage forms. The compounds of the present invention, especially Compound 2, can be administered in a wide variety of oral and parenteral dosage forms. In a particular embodiment, amorphous Compound 2 is formulated as a solid dosage form.

For preparing pharmaceutical compositions from the compounds of the present invention, pharmaceutically acceptable carriers can be either solid or liquid. For liquid formulations, the sodium salt and its solvates are used to obtain Compound 2 at a level of purity that is suitable for use in pharmaceutical compositions. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

In a particular embodiment the powders and tablets contain from five or ten to about seventy percent of the active compound. Suitable carriers are magnesium carbonate, magnesium stearate, steric acid, talc, sugar, lactose, pectin, dextrin, starch, gelatin, tragacanth, methylcellulose, sodium carboxymethylcellulose, microcrystalline cellulose, colloidal silicon dioxide, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The active agent may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active compound in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents. In some embodiments, where aqueous solubility and/or oral bioavailability is low, for example, with Compound 1, the compound may be formulated in a lipid containing formulation such as corn oil or formulated as a gel and delivered in a capsule.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compound according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredient may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

In a particular embodiment the pharmaceutical preparations are in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In particular embodiments, the pharmaceutical preparations are solid oral dosage forms such as tablets or capsules.

The invention will now be described with reference to the following Examples which illustrate some particular aspects of the present invention. However, it is to be understood that the particularity of the following description of the invention is not to supersede the generality of the preceding description of the invention.

EXAMPLES

Example 1

Classical Resolution of Racemate

A racemic mixture of Compound 1 and Compound 3 was obtained by the method of U.S. Pat. No. 5,246,943 and subjected to resolution using chiral salt formation. Twenty chiral bases were used to separate the enantiomers as chiral salts from racemic material, containing Compound 1 and Compound 3. The resolution procedure was to provide a salt of the enantiomer Compound 1 in a crystallized solid form, from which the free acid, Compound 1, could be prepared.

All the chiral bases were made up to 0.5 molar concentrations in ethanol. Those that would not dissolve in ethanol were added as solids, using the masses given, so that 1.05 molar equivalents of the bases were added to each sample of the free acid. The solutions were heated to 50° C. with stirring and cooled to 5° C. over twenty-one hours. The results are shown in Table 1. Samples 7 and 9 recrystallized on cooling. Those that did not recrystallize were sonicated for ten minutes, and then stored in a shaker at 25° C. overnight. Samples 4, 6, 12 and 19 were added as solids and did not dissolve fully at 50° C., so were matured at 25° C.

TABLE 1

Initial chiral salt resolution

| Sample | Chiral base | Volume used of 0.5M solution | Mass used | Solid |
|---|---|---|---|---|
| 1 | L-Arginine | Did not dissolve | 18.29 mg | — |
| 2 | (R)-(+)-N-Benzyl-α-methylbenzylamine | 210 μL | | — |
| 3 | (R)-(−)-2-amino-1-butanol | 210 μL | | — |
| 4 | (R)-(−)-Epinephrine | Did not dissolve | 19.24 mg | ✓ |
| 5 | (S)-(+)-2-Amino-3-methyl-1-butanol (valinol) | 210 μL | | — |
| 6 | (1S 2S)-2-Amino-1-(4-nitrophenyl)-1-3-propanediol | Did not dissolve | 22.51 mg | ✓ |
| 7 | (R)-(−)-amino-2-propanol | 210 μL | | ✓ |
| 8 | (−)-Cinchonidine | 210 μL | | — |
| 9 | (R)-(−)-1-Cyclohexylamine | 210 μL | | ✓ |
| 10 | Dehydroabietylamine | 210 μL | | — |
| 11 | (S)-(+)-Leucinol | 210 μL | | — |
| 12 | L-Lysine | Did not dissolve | 15.66 mg | ✓ |
| 13 | (R)-(+)-α-Methylbenzylamine | 210 μL | | — |
| 14 | (1R 2S)-(−)-N-Methylephedrine | 210 μL | | — |
| 15 | N-Methyl-D-glucamine | Did not dissolve | 20.70 mg | — |
| 16 | (R)-(−)-2-Phenylglycinol | 210 μL | | — |
| 17 | (S)-2-Pyrrolidinemethanol | 210 μL | | — |
| 18 | Quiniline | 210 μL | | — |
| 19 | (1R 2S)-(+)-Thiomicamine | Did not dissolve | 22.62 mg | ✓ |
| 20 | N-Ethyl-D-glucamine | Did not dissolve | 22.41 mg | — |

The six samples that gave solids were analyzed by chiral HPLC to assess any chiral resolution of the compound on salt formation and the results are shown in Table 2.

TABLE 2

Chiral HPLC analysis of salts.

| Sample | 4 | 6 | 7 | 9 | 12 | 19 |
|---|---|---|---|---|---|---|
| Solid | Impurities present | Impurities present | −0.5 | +3.0 | 0.0 | −8.0 |
| Liquor | 0.0 | Impurities present | Impurities present | +1.0 | +2.0 | +40.0 |

The material collected from Sample 19 from treatment with thiomicamine showed the greatest separation of the enantiomers. The solid isolated favoured Compound 1 over Compound 3, giving an enantiomeric excess of 8.0%. The liquor therefore favoured the enantiomer Compound 3, giving an enantiomeric excess of 40%. The analysis of the % of each enantiomer in the solid and liquor was analyzed and is shown in Table 3.

TABLE 3

Chiral HPLC results for the thiomicamine salt.

|  | % Compound 3 | Compound 1 |
|---|---|---|
| Sample 19 Solid | 46 | 54 |
| Sample 19 Liquor | 70 | 30 |

The solids collected were also analyzed by XRPD. Each of the solids collected gave new diffractograms that did not match either form of the free acid or the chiral base used to form the salt.

The thiomicamine salt was slurried at 25° C. overnight using 70 mg in 3 mL of ethanol, which was then filtered and the solid was analyzed by chiral HPLC, giving an increase in the enantiomeric excess, again in favour of Compound 1. This was repeated using 10 mg of the recovered solid in 600 $\mu$, of ethanol, giving an increase in enantiomeric excess of 77.8% of Compound 1. A $^1$H NMR after the first slurrying experiment shows the thiomicamine stays intact after this process, giving a 1:1 thiomicamine salt. The results are shown in Table 4.

TABLE 4

Chiral HPLC results of slurrying the thiomicamine salt.

|  | % Compound 3 | % Compound 1 | Enantiomeric excess |
|---|---|---|---|
| After first slurrying attempt | 31.9 | 68.1 | −36.2 |
| After second slurrying attempt | 11.1 | 88.9 | −77.8 |

Example 2

Further Chiral Resolution of Racemate

The racemic compound was dissolved in the appropriate solvent as set out in Table 5, using 50 mg of free acid in 500 $\mu$, of solvent. The chiral bases that did not dissolve fully in solution were added as solids to the free acid solution, so that all the solution contained 1.05 molar equivalents of the chiral base. The solutions were heated to 50° C. with stirring, and then cooled to 10° C. over twenty hours.

The solutions that did not produce a solid on cooling were placed in a sonicator for five minutes and left to stand at room temperature overnight. After this, only the solutions with L-arginine did not form a solid, from iso-propanol (IPA) or ethyl acetate (EtOAc).

TABLE 5

Second chiral salt resolution.

| Sample | Chiral base | Solvent | Volume used of 0.5M solution | Mass used | Solid formation |
|---|---|---|---|---|---|
| 1 | L-Arginine | IPA | 210 µL |  | no solid produced |
| 2 | (R)-(−)-2-amino-1-butanol | IPA | 210 Ml |  | solid formed on cooling |
| 3 | (R)-(−)-1-amino-2-propanol | IPA | 210 µL |  | solid formed on cooling |
| 4 | (R)-(−)-1-Cyclohexylethylamine | IPA | 210 µL |  | solid formed on cooling |
| 5 | L-Lysine | IPA | Did not dissolve | 15.66 mg | solid formed on cooling |
| 6 | (R)-(+)-α-Methylbenzylamine | IPA | 210 µL |  | solid formed after sonicator |
| 7 | N-Methyl-D-glucamine | IPA | Did not dissolve | 20.70 mg | solid formed on cooling |
| 8 | (1R 2S)-(+)-Thiomicamine | IPA | Did not dissolve | 22.62 mg | solid formed on cooling |
| 9 | N-Ethyl-D-glucamine | IPA | Did not dissolve | 22.41 mg | solid formed on cooling |
| 10 | (S)-(+)-2-Amino-1-propanol | IPA | 210 µL |  | solid formed on cooling |
| 11 | L-Arginine | Ethyl acetate | 210 µL |  | no solid produced |
| 12 | (R)-(−)-2-amino-1-butanol | Ethyl acetate | 210 µL |  | solid formed on cooling |
| 13 | (R)-(−)-1-amino-1-propanol | Ethyl acetate | 210 µL |  | solid formed on cooling |
| 14 | (R)-(−)-1-Cyclohexylethylamine | Ethyl acetate | 210 µL |  | solid formed on cooling |
| 15 | L-Lysine | Ethyl acetate | Did not dissolve | 15.66 mg | solid formed on cooling |
| 16 | (R)-(+)-α-Methylbenzylamine | Ethyl acetate | 210 µL |  | solid formed after sonicator |
| 17 | N-Methyl-D-glucamine | Ethyl acetate | Did not dissolve | 20.70 mg | solid formed on cooling |
| 18 | (1R 2S)-(+)-Thiomicamine | Ethyl acetate | Did not dissolve | 22.62 mg | solid formed on cooling |

TABLE 5-continued

Second chiral salt resolution.

| Sample | Chiral base | Solvent | Volume used of 0.5M solution | Mass used | Solid formation |
|---|---|---|---|---|---|
| 19 | N-Ethyl-D-glucamine | Ethyl acetate | Did not dissolve | 22.41 mg | solid formed on cooling |
| 20 | (S)-(+)-2-Amino-1-propanol | Ethyl acetate | 210 µL | | solid formed on cooling |

The solids were vacuum filtered and analyzed by chiral HPLC, as were the liquors collected. The results show there are a few bases that can be used to separate the enantiomers. Only one, thiomicamine, separated the enantiomers giving an excess of Compound 1, the desired enantiomer, in the solid. Therefore, these bases can be used to separate the enantiomers, however, thiomicamine has shown to be the only base to separate the enantiomers in both ethanol and ethyl acetate effectively and gives the desired enantiomer.

Methodology for Examples 3 to 15

X-Ray Powder Diffraction (XRPD)

Siemens D5000
XRPD patterns were collected on a Bruker AXS or Siemens D5000 diffractometer.

X-Ray Powder Diffraction patterns were collected on a Siemens D5000 diffractometer using CuKα radiation (40 kV, 40 mA), θ-θ goniometer, automatic divergence and receiving slits, a graphite secondary monochromator and a scintillation counter. The instrument was performance checked using a certified Corundum standard (NIST 1976).
Ambient Conditions Samples run under ambient conditions were prepared as flat plate specimens using powder as received. Approximately 35 mg of the sample was gently packed into a cavity cut into polished, zero-background (510) silicon wafer. The sample was rotated in its own plane during analysis. The details of the data collection are:
Angular range: 2 to 42° 2θ
Step size: 0.05° 2θ
Collection time: 4 s.step-1
Bruker AXS C2 GADDS X-Ray Powder Diffraction patterns were collected on a Bruker AXS C2 GADDS diffractometer using CuKα radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm.

The beam divergence, i.e., the effective size of the X-ray beam on the sample, was approximately 4 mm A θ-θ continuous scan mode was employed with a sample—detector distance of 20 cm which gives an effective 2θ range of 3.2°-29.7°. Typically the sample would be exposed to the X-ray beam for 120 seconds.
Ambient Conditions Samples run under ambient conditions were prepared as flat plate specimens using powder as received without grinding. Approximately 1-2 mg of the sample was lightly pressed on a glass slide to obtain a flat surface.

Non-Ambient Conditions

Samples run under non-ambient conditions were mounted on a silicon wafer with heat conducting compound. The sample was then heated to the appropriate temperature at ca. 20° C. min$^{-1}$ and subsequently held isothermally for about 1 minute before data collection was initiated.
Single Crystal X-Ray Diffraction (SCXRD)

Data were collected on a Bruker AXS 1K SMART CCD diffractometer equipped with an Oxford Cryosystems Cryostream cooling device. Structures were solved using either the SHELXS or SHELXD programs and refined with the SHELXL program as part of the Bruker AXS SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.
$^1$H NMR NMR spectra were collected on a Bruker 400 MHz spectrometer equipped with an auto-sampler. Samples were prepared in $d_6$-DMSO, unless otherwise stated.
Solid State $^{13}$C NMR NMR Spectra were collected on a Bruker Avance DRX-200 spectrophotometer. Samples were spun at 5 kHz in a 4 mm Bruker SB magic-angle spinning probe for $^{13}$C NMR at 50.3 MHz. Samples were packed into 4 mm $Z_nO$ NMR rotors and sealed with Kell-F caps. Proton transmitter power was increased to a value corresponding to a 90° pulse width of 2.8 µs for proton decoupling during $^{13}$C data acquisition. Transients were averaged over 1 h. Chemical shifts were referenced to an external reference using carbonyl resonance of glycine (176 ppm).
Differential Scanning Colorimetry (DSC)

DSC data were collected on a TA Instruments Q1000 equipped with a 50 position autosampler. The instrument was calibrated for energy and temperature calibration using certified indium.

Typically 0.5-3 mg of each sample, in a pin-holed aluminium pan, was heated at 10° C. min$^{-1}$ from 25° C. to 250° C. A nitrogen purge at 30 mL·min$^{-1}$ was maintained over the sample.
Thermo-Gravimetric Analysis (TGA)

TGA data were collected on a TA Instruments Q500 TGA, equipped with a 16 position autosampler. The instrument was temperature calibrated using certified Alumel.

Typically 5-30 mg of each sample was loaded onto a pretared platinum crucible and aluminium DSC pan, and was heated at 10° C. min$^{-1}$ from ambient temperature to 350° C. A nitrogen purge at 60 mL·min$^{-1}$ was maintained over the sample.
Gravimetric Vapour Sorption (GVS)

Sorption isotherms were obtained using a Hiden IGASorp moisture sorption analyzer, controlled by CFRSorp software.

The sample temperature was maintained at 25° C. by a Huber re-circulating water bath. The humidity was controlled by mixing streams of dry and wet nitrogen, with a total flow rate of 250 mL·min$^{-1}$. The relative humidity was measured by a calibrated Vaisala RH probe (dynamic range of 0-95% RH), located near the sample. The weight change, (mass relaxation) of the sample as a function of % RH was constantly monitored by the microbalance (accuracy ±0.001 mg).

Typically 10-20 mg of sample was placed in a tared mesh stainless steel basket under ambient conditions. The sample was loaded and unloaded at 40% RH and 25° C. (typical room conditions).

A moisture sorption isotherm was performed as outlined below (2 scans giving 1 complete cycle). The standard isotherm was performed at 25° C. at 10% RH intervals over a 0-90% RH range. Parameters are shown in Table 6:

TABLE 6

| Parameters | Values |
| --- | --- |
| Adsorption - Scan 1 | 40-90 |
| Desorption/Adsorption - Scan 2 | 85-Dry, Dry-40 |
| Intervals (% RH) | 10 |
| Number of Scans | 2 |
| Flow rate (mL · min$^{-1}$) | 250 |
| Temperature (° C.) | 25 |
| Stability (° C. · min$^{-1}$) | 0.05 |
| Minimum Sorption Time (hours) | 1 |
| Maximum Sorption Time (hours) | 4 |
| Mode | AF2 |
| Accuracy (%) | 98 |

The software uses a least squares minimization procedure together with a model of the mass relaxation, to predict an asymptotic value. The measured mass relaxation value must be within 5% of that predicted by the software, before the next % RH value is selected. The minimum equilibration time was set to 1 hour and the maximum to 4 hours.

The sample was recovered after completion of the isotherm and re-analyzed by XRPD.

Water Determination by Karl Fischer Coulometry (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determinations were made.

High Performance Liquid Chromatography (HPLC) Purity Determination

Purity analysis was performed on an Agilent HP1100 series system equipped with a diode array detector and using ChemStation software v9. Methods are shown in Tables 7 and 8.

TABLE 7

| Type of method | Normal Phase Isocratic | Reverse Phase Gradient | x x |
| --- | --- | --- | --- |
| Column: | Phenomenex Luna C18 (2), 150 × 4.6 mm, 5 μm | | |
| Column Temperature (° C.): | 25 | | |
| Injection (μL): | 10 | | |
| Detection: Wavelength, Bandwidth(nm): | 255, 90 nm bandwidth | | |
| Flow Rate (mL · min-1): | 1.0 | | |
| Phase A: | 0.1% TFA in water | | |
| Phase B: | 0.085% TFA in acetonitrile | | |
| Timetable: | Time (min) | % Phase A | % Phase B |
| | 0 | 95 | 5 |
| | 25 | 5 | 95 |
| | 25.2 | 95 | 5 |
| | 30 | 95 | 5 |

TABLE 8

| Chiral analysis | |
| --- | --- |
| Type of method | Normal Phase Reverse Phase x Isocratic Gradient x |
| Column: | Regis Technologies (S,S)-Whelk-01 10/100 Kromasil FEC 250 × 4.6 mm |
| Column Temperature (° C.): | 20 |
| Injection (μL): | 10 |
| Detection: Wavelength, Bandwidth (nm): | UV at 220 nm |
| Flow Rate (mL · min–1): | 2.0 |
| Mobile phase: | 60:40:0.1 n-Hexane:Ethanol:Acetic acid |
| Sample solvent: | 60:40 n-Hexane:Ethanol |

Ion Chromatography

Data were collected on a Metrohm 861 Advanced Compact IC using IC Net software v2.3. Samples were prepared as 1000 ppm stocks in water. Where sample solubility was low, a suitable solvent such as DMSO was used. Samples were diluted to 50 ppm or 100 ppm with an appropriate solvent prior to testing. Quantification was achieved by comparison with standard solutions of known concentration of the ion being analyzed. Conditions are shown in Tables 9A and 9B.

TABLE 9A

| Type of method | Anion exchange |
| --- | --- |
| Column: | Metrosep A Supp 5 - 250 (4.0 × 250 mm) |
| Column Temperature (° C.): | Ambient |
| Injection (μL): | 20 |
| Detection: | Conductivity detector |
| Flow Rate (mL · min$^{-1}$): | 0.7 |
| Eluent: | 3.2 mM sodium carbonate, 1.0 mM sodium hydrogen carbonate in water |

TABLE 9B

| Type of method | Cation exchange |
| --- | --- |
| Column: | Metrosep C 2 - 250 (4.0 × 250 mm) |
| Column Temperature (° C.): | Ambient |
| Injection (μL): | 20 |
| Detection: | Conductivity detector |
| Flow Rate (mL · min$^{-1}$): | 1.0 |
| Eluent: | 4.0 mM Tartaric acid, 0.75 mM Dipicolinic acid in water |

Example 3

Salt Selection

Compound 1 was dissolved in the solvent iso-propanol (IPA) or tetrahydrofuran (THF) as stated in Table 10 and had 1.05 molar equivalents of the pharmaceutically acceptable base added. The bases were prepared in a one molar solution, unless the base would not dissolve, in which case it was added as a solid. All solutions had 1.05 molar equivalents of the base added to them.

The solutions were stirred at 50° C. for two hours, and then cooled to 5° C. over three and a half hours with continued stirring. The samples were then stored at 5° C. for three days. Those that were still in solution were sonicated for ten minutes, and then if that gave no solids, the solvent was allowed to evaporate off slowly. All solids collected were analyzed by XRPD. The results are shown in Table 10.

TABLE 10

Results of the initial salt selection.

| Sample | Base | Solvent | Conc. and volume of solution used | Mass used | Cooling to 5° C. | Sonicated | Evaporated |
|---|---|---|---|---|---|---|---|
| 1 | Potassium hydroxide | IPA | 24.3 µL of 1M | | No solid | No solid | Gum |
| 2 | Sodium hydroxide | IPA | 24.3 µL of 1M | | No solid | No solid | Gum |
| 3 | L-Arginine | IPA | 48.7 µL of 0.5M | | No solid | No solid | Gum |
| 4 | Choline | IPA | 24.3 µL of 1M | | No solid | No solid | Gum |
| 5 | L-Lysine monohydrate | IPA | Added as solid | 4.00 mg | Crystalline | — | — |
| 6 | Dimethylaminoethanol | IPA | 24.3 µL of 1M | | No solid | No solid | Gum |
| 7 | N-Ethylglucamine | IPA | Added as solid | 5.09 mg | Amorphous | — | — |
| 8 | N-Methylglucamine | IPA | Added as solid | 4.75 mg | Amorphous | — | — |
| 9 | Tromethamine | IPA | Added as solid | 2.95 mg | Crystalline | — | — |
| 10 | Potassium hydroxide | THF | 24.3 µL of 1M | | No solid | No solid | Gum |
| 11 | Sodium hydroxide | THF | 24.3 µL of 1M | | No solid | No solid | Gum |
| 12 | L-Arginine | THF | 48.7 µL of 0.5M | | No solid | No solid | Gum |
| 13 | Choline | THF | 24.3 µL of 1M | | No solid | No solid | Gum |
| 14 | L-Lysine monohydrate | THF | Added as solid | 4.00 mg | Crystalline | — | — |
| 15 | Dimethylaminoethanol | THF | 24.3 µL of 1M | | No solid | No solid | Gum |
| 16 | N-Ethylglucamine | THF | Added as solid | 5.09 mg | No solid | No solid | Gum |
| 17 | N-Methylglucamine | THF | Added as solid | 4.75 mg | No solid | No solid | Gum |
| 18 | Tromethamine | THF | Added as solid | 2.95 mg | No solid | No solid | Gum |

Only three of the samples gave any solid crystalline material. The lysine salt from IPA and THF and the tromethamine salt from IPA. The XRPD analysis shows these all have different crystalline patterns. The HPLC chemical purity analysis of the lysine and tromethamine salts shows an improvement in the purity from the starting material, from 96.7% to 98.0% for the lysine salt and 97.8% for the tromethamine salt.

The crystalline lysine salt was shown to deliquesce at 40° C./75% RH and 25° C./94% RH. The tromethamine salt deliquesced at 25° C./94% RH. As a result, neither of these amine salts were suitable for pharmaceutical development.

Example 4

Further Salt Selection

The attempts to make a salt with potassium or sodium were repeated with different solvents. 20 mg of Compound 1 was dissolved in 20 µL of the appropriate solvent, to which 1.05 molar equivalents of potassium hydroxide or sodium hydroxide was added as a one molar solution in water. The solutions were heated to 50° C. for two hours and cooled to 5° C. over 21 hours, stirring throughout. If no solids formed after cooling the solutions were sonicated, then if still no solid formed, the solvent was allowed to evaporate to try to crystallize the salt.

TABLE 11

Results of the potassium/sodium salt formation

| Sample | Base | Solvent | Cooling to 5° C. | Sonicated | Evaporated |
|---|---|---|---|---|---|
| 1 | Potassium hydroxide | Ethyl acetate | No solid | No solid | Gum |
| 2 | Potassium hydroxide | Acetonitrile | No solid | No solid | Gum |
| 3 | Potassium hydroxide | Dioxane | No solid | No solid | Gum |
| 4 | Potassium hydroxide | Toluene | No solid | No solid | Gum |
| 5 | Potassium hydroxide | DCM | No solid | No solid | Gum |
| 6 | Sodium hydroxide | Ethyl acetate | No solid | No solid | Gum |
| 7 | Sodium hydroxide | Acetonitrile | No solid | No solid | Gum |
| 8 | Sodium hydroxide | Dioxane | No solid | No solid | Gum |
| 9 | Sodium hydroxide | Toluene | No solid | No solid | Gum |
| 10 | Sodium hydroxide | DCM | No solid | No solid | Gum |

There was no solvent in which the solution gave a solid, only gums were produced.

The gums were used to slurry in a new set of solvents in an attempt to generate crystalline material. 100 µL of the solvent was added to the gum and put for maturation overnight on a cycle between 50° C. for four hours, then room temperature for four hours. Any solids were filtered and analyzed by XRPD. The results are shown in Table 12.

TABLE 12

Results of the slurrying of potassium/sodium salts.

| Sample | Base | Solvent | After maturation |
|---|---|---|---|
| 1 | Potassium hydroxide | Acetone | No solid |
| 2 | Potassium hydroxide | IPA | No solid |
| 3 | Potassium hydroxide | THF | No solid |
| 4 | Potassium hydroxide | Ethanol | No solid |
| 5 | Sodium hydroxide | Acetone | No solid |
| 6 | Sodium hydroxide | IPA | Crystalline solid |
| 7 | Sodium hydroxide | THF | No solid |
| 8 | Sodium hydroxide | Ethanol | Crystalline solid |

The solids from IPA and ethanol gave new crystalline patterns from the XRPD analysis. The XRPD peaks and their intensities are shown in Tables 13 and 14.

TABLE 13

XRPD peaks for Compound 4.

| Angle 2θ | Intensity % |
|---|---|
| 5.5 | 40.1 |
| 6.7 | 9.9 |
| 8.0 | 100.0 |
| 8.7 | 42.4 |
| 9.3 | 35.7 |
| 11.1 | 6.2 |
| 13.4 | 79.4 |
| 14.3 | 14.6 |
| 14.7 | 7.8 |
| 15.8 | 11.7 |
| 16.1 | 20.0 |
| 16.6 | 11.7 |
| 17.4 | 48.5 |
| 17.8 | 17.2 |
| 18.8 | 35.7 |
| 20.3 | 16.9 |
| 20.9 | 20.1 |
| 21.4 | 24.9 |
| 22.2 | 27.0 |
| 22.8 | 23.5 |
| 24.2 | 22.7 |
| 25.4 | 22.9 |
| 26.9 | 15.8 |
| 27.6 | 9.5 |
| 28.7 | 10.0 |
| 29.7 | 17.6 |
| 30.3 | 13.1 |
| 31.3 | 12.3 |
| 32.1 | 12.4 |
| 33.5 | 10.7 |
| 35.7 | 16.8 |
| 41.0 | 12.8 |

TABLE 14

XRPD peaks for Compound 5.

| Angle 2θ | Intensity % |
|---|---|
| 5.4 | 38.1 |
| 6.6 | 12.0 |
| 7.9 | 100.0 |
| 8.6 | 40.6 |
| 9.2 | 25.1 |
| 10.8 | 13.8 |
| 13.4 | 68.0 |
| 14.0 | 20.0 |
| 15.9 | 42.1 |
| 16.4 | 25.9 |
| 17.3 | 70.1 |
| 17.6 | 48.7 |
| 18.6 | 93.5 |
| 20.0 | 78.1 |
| 20.5 | 63.1 |
| 21.1 | 53.8 |
| 21.9 | 94.2 |
| 22.5 | 53.6 |
| 23.0 | 35.9 |
| 24.0 | 57.7 |
| 25.0 | 81.2 |
| 25.5 | 38.8 |
| 26.0 | 39.1 |
| 26.6 | 53.4 |
| 27.2 | 27.1 |
| 28.3 | 20.6 |
| 29.3 | 21.5 |

Analysis by ion chromatography showed the solid to contain one mole of sodium. $^1$H NMR confirmed the presence of solvent and chiral HPLC analysis show that no significant degradation had occurred and it was still the pure enantiomer Compound 1. When analyzed by variable temperature XRPD, the crystal structure broke down after heating above 135° C. Attempts to make the sodium salt in IPA and ethanol by slow cooling, seeding, evaporation of solvent and maturation all failed. The sodium salt solvates were placed at 40° C./75% RH for one week, which gave a new XRPD trace, identified as a trihydrate by a 10% weight loss on the TGA, equating to three moles of water, and the removal of the solvent, either ethanol or IPA.

Example 5

Sodium Salt Studies

In an attempt to form the sodium salt ethanol solvate directly, Compound 4, without crystallization from a gum, the salt was prepared using sodium ethoxide in ethanol instead of using sodium hydroxide in water. It was thought that the presence of water in the initial preparation may have prevented crystallization.

25 mg of Compound 1 was dissolved in 50 μL ethanol at room temperature. 18.4 μL, 1.0 equivalent, of sodium ethoxide (21% in ethanol). Solid material rapidly crystallized on standing at room temperature. The sample filtered under vacuum and dried at 25° C. under vacuum for one day. The XRPD and TGA analysis shows the material produced is the mono-ethanol solvate (Compound 4). This material was stored at 40° C./75% RH overnight forming the hydrate (Compound 6), for further analysis.

The hydrate, Compound 6, was identified again by XRPD. The XRPD peaks and their intensities are shown in Table 15.

TABLE 15

XRPD peaks for Compound 6.

| Angle 2θ | Intensity % |
|---|---|
| 4.8 | 95.1 |
| 5.5 | 14.4 |
| 7.3 | 29.5 |
| 8.3 | 21.3 |
| 9.9 | 35.4 |
| 12.0 | 43.3 |
| 12.6 | 44.1 |
| 15.2 | 63.7 |
| 16.7 | 100 |
| 17.2 | 92.6 |
| 17.9 | 61.3 |
| 19.0 | 76.8 |
| 21.5 | 62.3 |
| 23.5 | 66.4 |
| 24.5 | 66.1 |

When analyzed by variable temperature XRPD, the material lost crystallinity when heated above 70° C.

The GVS analysis of Compound 6 showed the material was losing some weight, 2%, before the analysis started, when stored at 40% RH. The weight increased gradually to +6% weight when taken up to 90% RH, then lost again when taken down to 0% RH, reaching −12% weight. On returning to 40% RH, the material reached −6% weight. This cycle of gradually increasing in weight to +6% by 90% RH, then dropping to −12% at 0% RH and ending at −6% weight at 40% RH was repeated. There were no plateaus where the weight was stable at a range of humidities. The GVS pattern suggests the water may be able to enter or leave the crystal lattice depending on the relative humidity of the atmosphere around it, giving a percentage water content for the specific relative humidity of the atmosphere in which the material in contained. So, if the humidity is higher, at 75% RH, Compound 6, was formed, however, when the humidity is lower, at 40% RH, Compound 7, was formed. The estimation of a dihydrate when removed from the GVS at 40% RH is supported by the TGA thermogram giving a weight loss of 6.6%, equating to two moles of water. The XRPD trace after GVS analysis matched the trace of the material before GVS analysis, so the transfer of water between the crystal and the atmosphere has not altered the crystal structure.

A sample of Compound 6 removed from 40° C./75% RH was dried at 40° C., with no vacuum, for four days. This material gave the same XRPD trace after drying, but when analyzed by TGA, the material showed a weight loss of 6.6%, again giving us the dihydrate, Compound 7. This supports the GVS as the material was stored at 40° C., but still at the ambient relative humidity of 40%. Four moles of water is 12.3% by weight, three moles is 9.25% and two moles is 6.2%. The XRPD peaks and intensities for Compound 7 are shown in Table 16.

TABLE 16

| XRPD peaks for Compound 7. | |
|---|---|
| Angle 2θ | Intensity % |
| 4.8 | 100.0 |
| 5.5 | 17.5 |
| 7.3 | 23.7 |
| 8.2 | 16.9 |
| 12.1 | 71.4 |
| 12.8 | 25.3 |
| 15.8 | 75.1 |
| 16.9 | 95.0 |
| 18.2 | 86.2 |
| 19.3 | 84.8 |
| 25.6 | 61.7 |

Subsequent DSC-TGA analysis of Compound 6 gave a 13% weight loss suggesting that Compound 6 may have 4 molecules of water or 4+ fractional molecules of water. Subsequent DSC-TGA analysis of Compound 7 gave a 5.5% weight loss suggesting that Compound 7 may be a fractional hydrate with less than 2 molecules of water. In these subsequent DSC-TGA studies, the data was obtained on a SDT Q600 Instrument starting at ambient temperature and increasing to about 300° C. at 10° C. per minute.

Example 6

Sodium Salt Hydrates

The sodium salt hydrate was prepared only by exposure to high humidities, so a series of experiments were set up to convert the sodium salt solvates to the hydrate by means of crystallizing the hydrate from solution.

The IPA and ethanol solvates of the salt were slurried in water, using 25 mg of the salt in 100 μL of water, slurried at 25° C., which recrystallized a material giving a new trace by XRPD of 99.1% chemical purity when analyzed by HPLC. The TGA analysis showed a weight loss of 25%, which began losing weight immediately when heating started. Ion chromatography showed the new crystal formed was a hemi-sodium salt. This material is less favourable than the previous hydrate observed, so continued effort was made to form the previous hydrate by slurrying. The XRPD peaks and intensities for the hemi-sodium salt hydrate are shown in Table 17.

TABLE 17

| XRPD peaks for hemi sodium salt hydrate | |
|---|---|
| Angle 2θ | Intensity % |
| 6.2 | 9.2 |
| 7.8 | 15.6 |
| 8.7 | 13.6 |
| 10.1 | 26.0 |
| 12.1 | 21.8 |
| 12.7 | 22.8 |
| 13.7 | 24.8 |
| 15.6 | 43.4 |
| 16.1 | 28.9 |
| 16.9 | 27.2 |
| 18.5 | 44.9 |
| 19.8 | 48.3 |
| 20.9 | 60.5 |
| 21.3 | 50.7 |
| 22.4 | 62.6 |
| 23.4 | 69.5 |
| 24.4 | 100.0 |
| 25.1 | 79.6 |
| 25.5 | 69.0 |
| 26.3 | 75.3 |

The ethanol solvate of the sodium salt was used to try to form the hydrate by slurrying in ethanol or IPA with varying proportions of water.

The precipitates formed from slurries in 75% water solutions, gave the same XRPD trace as the material that was slurried in 100% water, giving the hemi-sodium salt. One sample that gave a new crystalline XRPD pattern and was slurried in 10% water in ethanol. This sample was sent for single crystal analysis, which proved the material to be a hemi-sodium salt mono-ethanolate.

Another attempt was made to form the hydrated sodium salt from the ethanol solvate of the sodium salt. 25 mg of the ethanol solvate of sodium salt, Compound 4, was weighed into each vial, to which the appropriate solvent containing 1% water was added. The solvent was added 10 μL at a time to ensure the material made a slurry, before being placed in the maturation chamber, cycling four hours at 50° C. and four hours at room temperature. The samples were seeded with the previously formed hydrated sodium salt. If no solid formed when retrieved from the maturation chamber they were stored at 5° C. to encourage crystallization. If there was no solid after three days at 5° C., the anti-solvent, heptane, was added drop-wise and the solutions placed back into the maturation chamber. The results are shown in Table 18.

TABLE 18

| Results of slurrying in 1% aqueous solutions. | | | | | |
|---|---|---|---|---|---|
| Sample | Solvent | Volume of solvent used | After maturation | Stored at 5° C. | Anti-solvent added |
| 1 | Acetone | 30 μL | No solid | No solid | Crystalline solid matching ethanol solvate |

TABLE 18-continued

Results of slurrying in 1% aqueous solutions.

| Sample | Solvent | Volume of solvent used | After maturation | Stored at 5° C. | Anti-solvent added |
|---|---|---|---|---|---|
| 2 | THF | 30 μL | No solid | No solid | Crystalline solid matching ethanol solvate |
| 3 | Acetonitrile | 30 μL | No solid | No solid | Gum |
| 4 | MIBK | 30 μL | Gum | n/a | n/a |
| 5 | MEK | 30 μL | Crystalline solid matching MEK solvate | n/a | n/a |
| 6 | Ethyl acetate | 40 μL | Crystalline solid matching ethanol solvate | n/a | n/a |
| 7 | Dioxane | 70 μL | No solid | Crystalline solid not the hydrate | n/a |

The material collected was filtered and analyzed by XRPD. The sample from methylethylketone (MEK) gave a diffractogram not previously seen and so likely to be the MEK solvate. The sample from ethyl acetate, THF and acetone gave the XRPD diffractogram pattern matching the ethanol solvate starting material. The material collected from dioxane gave a new trace, not seen previously, so is likely to be a dioxane solvate. The remaining two samples gave only gums.

Example 7

Polymorphism of the Mono-Sodium Salt (Compound 2)

Approximately 30 mg of the mono-ethanolate sodium salt (Compound 4) was added to each of fifteen vials. 200 μL of the appropriate solvent was added, noting the solubility at room temperature. If the material dissolved fully it was placed at 5° C., if not fully dissolved, was placed at 50° C. All vials were then stored at 5° C. for 16 hours. The solutions that gave a solid were analyzed by XRPD, those that remained a solution were allowed to evaporate slowly at ambient conditions. The results are shown in Table 19.

Seven of the samples, Samples 7, 10, 11, 12, 13, 14 and 15, gave a solid, which were analyzed by XRPD. The XRPD diffractograms of these seven samples gave three new patterns from acetonitrile, MEK and 100% EtOAc, which had a matching pattern to the sample from tert-butylmethylketone (TBME). The samples from heptane and 1-propanol gave the same pattern as the ethanol solvate and the sample from 10% water in EtOAc gave the same pattern as the hemi-sodium salt. Samples 10, 11, 13 and 14 were dried at 25° C. under vacuum for one hour, then analyzed by $^1$H NMR, which showed Sample 10 retained minimal solvent indicating it to be a crystalline non-solvated form of the sodium salt. This sample was investigated further, being analyzed by GVS, TGA, DSC and all four of these samples being stored at 40° C./75% RH, followed by further XRPD analysis. The XRPD peaks and intensities for the non-solvated sodium salt (Compound 2) are shown in Table 20.

TABLE 20

XRPD peaks for Compound 2.

| Angle (2-theta) | Intensity % |
|---|---|
| 5.5 | 49.1 |
| 6.0 | 18.6 |
| 6.9 | 7.4 |

TABLE 19

Results of the polymorphism screen.

| Expt No. | Solvent | water content added | weight (mg) | Solubility at 25° C. in 200 μL | Solubility at 50° C. | Solubility at 5° C. after 16 hrs | After Evaporation |
|---|---|---|---|---|---|---|---|
| 1 | Acetone | 10% | 30 | ✓ | n/a | solution | |
| 2 | Ethanol | 10% | 33 | ✓ | n/a | solution | |
| 3 | THF | 10% | 33 | ✓ | n/a | solution | |
| 4 | MeCN | 10% | 34 | ✓ | n/a | solution | |
| 5 | MEK | 10% | 30 | ✓ | n/a | solution | |
| 6 | 1-propanol | 10% | 33 | ✓ | n/a | solution | |
| 7 | EtOAc | 10% | 31 | ✓ | n/a | ppte | n/a |
| 8 | Acetone | — | 32 | ✓ | n/a | solution | gum |
| 9 | THF | — | 34 | ✓ | n/a | solution | gum |
| 10 | MeCN | — | 33 | ✓ | n/a | solution | ppte |
| 11 | MEK | — | 32 | ✓ | n/a | ppte | n/a |
| 12 | 1-propanol | — | 33 | x (slurry) | x (slurry) | ppte | n/a |
| 13 | EtOAc | — | 34 | x (slurry) | ✓ | ppte | n/a |
| 14 | TBME | — | 32 | x (slurry) | x (slurry) | ppte | n/a |
| 15 | heptane | — | 34 | x (slurry) | x (slurry) | ppte | n/a |

TABLE 20-continued

XRPD peaks for Compound 2.

| Angle (2-theta) | Intensity % |
|---|---|
| 8.5 | 10.0 |
| 9.6 | 34.0 |
| 11.0 | 57.7 |
| 13.3 | 38.9 |
| 14.0 | 16.2 |
| 16.1 | 18.7 |
| 16.7 | 35.8 |
| 17.9 | 28.1 |
| 18.4 | 57.1 |
| 19.6 | 29.3 |
| 20.6 | 100.0 |
| 21.8 | 29.4 |
| 22.3 | 39.1 |
| 23.3 | 27.1 |
| 23.9 | 23.3 |

The material from acetonitrile (MeCN) showed a weight loss of 3.5% on the TGA, which was lost gradually until about 120° C., when the weight was lost more rapidly, coinciding with an endotherm observed from the DSC representing the melting of the crystalline form. The GVS analysis showed a rise in weight of about 17% from 40% RH to 90% RH, which then dropped to a weight of −2% at 0% RH, dropping a total of 19% weight. The weight gained 6% by 40% RH, matching the weight increase observed from the hydrate, not returning to the weight of the material as it entered. The repeated cycle matched that of the cycle of the hydrate and the XRPD diffractogram of the material after GVS analysis showed it to be the hydrated form of the salt. This was observed as well by the XRPD diffractogram of the other three samples after they were stored at 40/75% RH.

Example 8

Potassium Salt of Compound 1

The procedure for forming the sodium salt, using sodium ethoxide, was repeated using potassium ethoxide. 25 mg of the amorphous free acid, Compound 1, was dissolved in 50 µL ethanol. 22 µL of potassium ethoxide (24% in ethanol), one molar equivalent, was added and the solution stored in a shaker at 25° C. for three days. With no solid precipitating, the vial was placed in a sonicator for five minutes, then stored at 5° C. to try to induce crystallization of a potassium salt. This was repeated, using a range of different solvents to dissolve the free acid. The results are shown in Table 21.

TABLE 21

Results of the potassium salt formation.

| Sample | Solvent | Storage in the shaker at 25° C. | Sonication | Stored at 5° C. | Maturation with anti-solvent |
|---|---|---|---|---|---|
| 1 | Methanol | No solid | No solid | No solid | Oil |
| 2 | IPA | No solid | No solid | No solid | Gum |
| 3 | THF | No solid | No solid | No solid | Gum |
| 4 | Ethyl acetate | No solid | No solid | No solid | Gum |
| 5 | Acetonitrile | No solid | No solid | No solid | Oil |
| 6 | Dioxane | No solid | No solid | No solid | Gum |
| 7 | Toluene | No solid | No solid | No solid | Amorphous |
| 8 | DCM | No solid | No solid | No solid | Gum |
| 9 | Acetone | No solid | No solid | No solid | Gum |
| 10 | Water | No solid | No solid | No solid | Oil |

None of the solvents used gave a precipitate throughout the experiments. In a further attempt to try to get the potassium salt to crystallize, the solvent was allowed to evaporate slowly, giving only gums from all the samples. The gums were re-dissolved in 200 µL of the same solvent at 50° C., then heptane, the anti-solvent, was added drop-wise to give some precipitate, which was then stored in a maturation chamber, cycling between 50° C. for four hours and room temperature for four hours. All of the samples filtered to give gums or oils, except for one sample from toluene, which, when analyzed by XRPD, gave an amorphous curve, but with small peaks within it. The sample from toluene had 50 µL of toluene added to it and was returned to the maturation chamber for an extra four days, after which time the sample was re-analyzed by XRPD, showing a slight improvement of the peaks on the diffractogram, but was still mainly amorphous.

To investigate the sample from toluene, the salt formation was repeated on a larger scale. 50 mg of the free acid, Compound 1, (purified via the sodium salt) was dissolved in 400 µL of toluene, to which 44 µL of potassium ethoxide (24% weight in ethanol) was added. Heptane was added drop-wise to the solution until some precipitate was observed and the vial was placed in the maturation chamber, cycling between 50° C. for four hours and room temperature for four hours. The material collected was filtered, but formed a gum on standing.

Example 9

Calcium and Magnesium Salts of Compound 1

The mono-ethanolate sodium salt of Compound 2 was used in an attempt to exchange the sodium ion with a calcium or a magnesium ion. 50 mg of the sodium salt was dissolved in an IPA/water mixture. 5.47 mg of calcium chloride and 4.70 mg of magnesium chloride were dissolved in 11 mL and 9 mL of methanol respectively. The calcium chloride solution and the magnesium chloride solution were each added to a solution of 50 mg of the sodium salt and stirred for three hours, then stored at 5° C. overnight.

The solution was placed on the rotary evaporator to remove the solvent, leaving a solid. Water was added to remove any sodium chloride that may have been present and the material was filtered.

The magnesium sample gave a gum, but the calcium sample gave an amorphous solid, by XRPD analysis. This was analyzed by $^1$H NMR and ion chromatography. The $^1$H NMR showed the same peaks as previously observed for the free acid. The ion chromatography results show the material only contained 0.07 equivalents of the calcium ion in the sample, which should have been 0.5 if the calcium salt had formed. The amorphous material must have been the amorphous free acid Compound 1 with a minimal amount of calcium chloride remaining in the sample as a mixture.

Example 10

Conversion of Sodium Salt to Free Acid

Amorphous Compound 2 (5.00 g, 8.59 mmol) was dissolved in ethyl acetate (50 mL) and washed with 1M HCl (30 mL), dried with $MgSO_4$ and evaporated to give a yellow foam. this foam was dried under high vacuum at 50° C. for 2 hours giving 4.373 g yellow foam (100%). Integration of the signals at δ 1.25, 2.39 and 2.87 in the $^1$H NMR spectrum suggested 2.6% w/w ethyl acetate remained trapped in the foam. HPLC analysis shows a purity of 97.1%. Chiral HPLC indicates the sample is in >98% enantiomeric excess.

m/z (ES⁻) 506.2 [MH⁺, 100%], 507.2 [$^{13}$C-MH⁺, 40%]; HRMS $C_{32}H_{28}NO_5$ requires 506.1967. found 506.1964. $^1$H NMR (CDCl$_3$, 500 MHz) δ 2.39 (1H*, dd, J 16.3, 6.0), 2.87 (1H, dd, J 16.3, 6.2), 3.32 (1H, dd, J 16.2, 4.8), 3.39 (1H* dd, J 16.2, 2.4), 3.81 (3H*, s), 3.81 (3H, s), 4.42 (1H, d, J 14.9), 4.49 (1H*, d, J 17.2), 4.58 (1H, d, J 14.9), 4.82 (2H*, m), 4.89 (1H, d, J 10.9), 4.95 (2H*, m), 5.01 (1H, d, J 11.0), 5.15 (1H, 1H*, m), 5.31 (1H, s), 6.54 (1H, d, J 8.4), 6.70 (1H, d, J 8.4), 6.78 (1H*, d, J 8.5), 6.84 (1H*, d, J 8.5), 7.10-7.41 (15H, 15H*, m). $^{13}$C NMR (CDCl$_3$, 125 MHz) 24.9, 25.8*, 43.3*, 45.6, 52.4, 54.4*, 55.5, 55.6*, 55.9, 60.4*, 74.8*, 74.9, 111.2, 111.7*, 121.4, 122.2*, 125.3, 125.6, 125.7, 127.0, 127.1, 127.2, 127.2, 127.4, 128.0, 128.2, 128.3, 128.4, 128.5, 128.6, 128.6, 128.6, 128.8, 129.0, 129.1, 129.2, 129.4, 137.4, 137.6*, 138.3*, 138.8, 138.9, 139.2*, 145.0, 151.1*, 151.8, 171.9*, 172.5, 175.4, 175.5. [α]$_D$+5.1 (DCM, c0.68); IR (cm$^{-1}$, KBr disc), 3439, 3029, 1737, 1621, 1496, 1454, 1275, 1215, 1093, 1050, 895, 803, 747, 700, 632. * denotes minor rotamer.

Example 11

Recrystallization of Free Acid

The free acid (Compound 1) formed in Example 10 was added to ten vials, 25 mg in each, to which 15 μL of the appropriate solvent was added and placed in a maturation chamber cycling four hours at 50° C. and four hours at room temperature for three days. After this time, those that did not recrystallize were sonicated, then if still no solid formed, were stored at 5° C. The results are shown in Table 22.

TABLE 22

Results of the recrystallization of the free acid.

| Sample | Solvent | Slurrying over three days | Sonication | Stored at 5° C. | Maturation with anti-solvent |
|---|---|---|---|---|---|
| 1 | Ethanol | No solid | No solid | No solid | Gum |
| 2 | IPA | No solid | No solid | No solid | Gum |
| 3 | THF | No solid | No solid | No solid | Gum |
| 4 | Ethyl acetate | No solid | No solid | No solid | Gum |
| 5 | Acetonitrile | No solid | No solid | No solid | Oil |
| 6 | Dioxane | No solid | No solid | No solid | Gum |
| 7 | Toluene | No solid | No solid | No solid | Gum |
| 8 | DCM | No solid | No solid | No solid | Gum |
| 9 | Acetone | No solid | No solid | No solid | Oil |
| 10 | Water | No solid | No solid | No solid | Amorphous |

None of the solutions recrystallized any solid material, so the solvents were allowed to evaporate slowly, however, this gave only gums. 200 μL of the same solvent was added to each vial and heated to 50° C. to dissolve the gum. Heptane was added to the solution until some precipitate was observed, then the vial was placed in the maturation chamber. All of the samples gave either a gum or an oil, except for one, from water, which gave an amorphous solid when analyzed by XRPD.

Example 12

Attempted Recrystallization of Free Acid from Sodium Salt

A procedure to prepare an amorphous form of Compound 1 from the α-methylbenzylamine salt is described in U.S. Pat. No. 5,246,943 (1992) which involves the addition of aqueous potassium bisulphate solution to a methanol solution of the α-methylbenzylamine salt of Compound 1. This technique of preparing the free acid form of Compound 1 by precipitation with potassium bisulphate solution was used in an attempt to characterize the physical form of the resulting free acid when this technique was applied to the sodium salt (Compound 2). 50 mg of the sodium salt was dissolved in a minimum volume of methanol and a solution of potassium bisulfate, in methanol (excess of 1% potassium bisulfate), was added drop-wise to precipitate the free acid. The vial was placed in the maturation chamber, alternating between 50° C. and room temperature for four hours each, for three days. The sample was filtered and the XRPD diffractogram showed the material collected was amorphous; however, there were some peaks in the diffractogram caused by some of the remaining inorganic material.

Example 13

Stability of Ethanol Solvate to Varying Humidity

A sample of the ethanol solvate was placed at 40° C./75% RH overnight to form the sodium salt trihydrate. This conversion was checked by XRPD before proceeding to use the hydrated form. About 600 mg was prepared.

The material was split into six batches of 90 mg and stored at six different temperatures and humidities. The humidities were fixed by storing the material in a container above a saturated solution of one of potassium acetate, potassium carbonate or sodium nitrite stored at either 40° C. or 25° C. This gives the six temperature and humidity conditions stated in Table 23 below. The material was analyzed by XRPD, HPLC and coulometric Karl Fischer after one, seven and fourteen days.

TABLE 23

Results of the humidity stability assessment.

| | | | | One day | | | Seven days | | | 14 days | | |
|---|---|---|---|---|---|---|---|---|---|---|---|---|
| Sample | Saturated solution | Temp | Relative humidity | XRPD | HPLC | Karl Fischer | XRPD | HPLC | Karl Fischer | XRPD | HPLC | Karl Fischer |
| 1 | Potassium acetate | 25° C. | 22% | Slight change in peaks (2) | 97.7% | 7.6% | No change from prev. (2) | 96.2% | 10.2% | No change from prev. (2) | 97.6% | 9.5% |
| 2 | Potassium acetate | 40° C. | 20% | Slight change in peaks (2) | 97.7% | 6.7% | No change from prev. (2) | 97.1% | 8.7% | No change from prev. (2) | 97.8% | 8.1% |

TABLE 23-continued

Results of the humidity stability assessment.

| | | | | One day | | | Seven days | | | 14 days | | |
|---|---|---|---|---|---|---|---|---|---|---|---|---|
| Sample | Saturated solution | Temp | Relative humidity | XRPD | HPLC | Karl Fischer | XRPD | HPLC | Karl Fischer | XRPD | HPLC | Karl Fischer |
| 3 | Potassium carbonate | 25° C. | 43% | No change (1) | 97.9% | 13.0% | No change (1) | 97.7% | 14.2% | No change (1) | 96.8% | 13.5% |
| 4 | Potassium carbonate | 40° C. | 42% | No change (1) | 97.3% | 10.6% | Slight change in peaks (2) | 97.5% | 13.1% | No change from prev. (2) | 97.5% | 9.4% |
| 5 | Sodium nitrite | 25° C. | 65% | No change (1) | 97.0% | 15.4% | No change (1) | 97.0% | 14.1% | No change (1) | | *11.6%, 24.6% |
| 6 | Sodium nitrite | 40° C. | 62% | No change (1) | 97.7% | 16.9% | No change (1) | 97.3% | 14.8% | No change (1) | | 14.9% |

*The coulometric Karl Fischer analysis gave a different result on the second run, so both results are displayed instead of a mean figure.

The material was made into the hydrate by storing at 40° C./75% RH, so those stored at the lower humidity, about 60% RH remained the same material, without any changes in the XRPD diffractogram, keeping a high value of water content throughout. The material stored at the low humidities, around 20% RH, dropped in water content overnight, giving a slight change in one of the peaks on the XRPD diffractogram. One peak at 12 2-theta went from being a double peak to having a single peak. This difference in the XRPD diffractogram was apparent in all the material that lost water content. The material stored at about 40% RH lost water only when heated at 40° C. over a week. At 25° C. however, the water content, and therefore the XRPD diffractogram, remained the same throughout the two weeks. The purity of the material was maintained throughout the experiment and does not seem to be effected by storage at low or high humidities.

Example 14

Compound 2 Solubility and Stability

Solubility of Compound 2 in a solvent, selected from water, methanol, acetonitrile (ACN) and iso-propanol and in 50 mM phosphate buffer at pH 1, 2, 7 and 8, 50 mM citrate buffer at pH 3, 4, 5 and 6 and in 50 mM borate buffer at pH 9 was assessed.

Compound 2 was added to 10 mL of the solvent or buffer until the solution was visibly saturated and remained cloudy upon vortex mixing. Each sample was placed on a reciprocal shaker at room temperature for 24 hours then filtered through a 0.45 μm nylon filter to remove excess suspended compound.

The samples were then diluted where required in accordance with Table 24, and analyzed by HPLC. The results were compared with a standard curve of known concentrations in ACN. The results are shown in Table 25.

TABLE 24

Stock Sample Dilutions for t = 0 and t = 1 week.

| Sample | Volume of Stock Solution (mL) | Total Volume of Selected Media (mL) |
|---|---|---|
| H₂O | 1 | 50 |
| H₂O | 1 | 25 |
| MeOH | 1 | 100 |
| ACN | 1 | 25 |
| IPA | 1 | 25 |
| pH 1 | N/A | N/A |
| pH 2 | N/A | N/A |
| pH 3 | N/A | N/A |

TABLE 24-continued

Stock Sample Dilutions for t = 0 and t = 1 week.

| Sample | Volume of Stock Solution (mL) | Total Volume of Selected Media (mL) |
|---|---|---|
| pH 4 | N/A | N/A |
| pH 5 | N/A | N/A |
| pH 6 | 1 | 10 |
| pH 7 | 1 | 10 |
| pH 8 | 1 | 10 |
| pH 9 | 1 | 10 |

TABLE 25

Compound 2 Solution Solubility

| Solvent | Solubility |
|---|---|
| pH 1 buffer (phosphate, 50 mM) | <1 μg/mL |
| pH 2 buffer (phosphate, 50 mM) | <1 μg/mL |
| pH 3 buffer (phosphate, 50 mM) | <1 μg/mL |
| pH 4 buffer (citrate, 50 mM) | <1 μg/mL |
| pH 5 buffer (citrate, 50 mM) | 33 μg/mL |
| pH 6 buffer (citrate, 50 mM) | 0.9 mg/mL |
| pH 7 buffer (phosphate, 50 mM) | 1.7 mg/mL |
| pH 8 buffer (phosphate, 50 mM) | 1.6 mg/mL |
| pH 9 buffer (borate, 50 mM) | 5.3 mg/mL |
| Water | 14 mg/mL |
| Methanol | >50 mg/mL |
| Acetonitrile | 12 mg/mL |
| IPA | 0.7 mg/mL |

The above analysis was taken as t=0 and the samples were then divided in two and one of each sample was stored at 5° C. for one week and the other of each sample was stored at 25° C./60% relative humidity (RH) for one week.

After one week, the samples were allowed to equilibrate to room temperature and if required (H₂O and pH 7-9 samples stored at 5° C.) refiltered to remove precipitate.

The samples were reanalyzed by HPLC. The results are shown in Tables 26 and 27.

TABLE 26

Compound 2 Solution Stability at 25° C./60% RH

| | % Purity | | |
|---|---|---|---|
| Sample | Initial % Purity | t = 1 week % Purity at 25° C./60% RH | Δ% Purity at 25° C./60% RH |
| H₂O | 95.58 | 95.67 | +0.09 |
| MeOH | 97.39 | 97.39 | 0.00 |
| ACN | 97.50 | 97.46 | −0.04 |
| IPA | 89.28 | 90.51 | +1.23 |
| pH 1* | — | — | — |
| pH 2* | — | — | — |
| pH 3* | — | — | — |
| pH 4* | — | — | — |
| pH 5* | — | — | — |
| pH 6 | 88.37 | 88.98 | +0.61 |
| pH 7 | 76.12 | 76.52 | +0.40 |
| pH 8 | 85.54 | 86.70 | +1.16 |
| pH 9 | 91.24 | 91.60 | +0.36 |

*Due to the low solubility of the pH 1-5 solutions, no stability data could be determined

TABLE 27

Compound 2 Solution Stability at 5° C.

| | % Purity | | |
|---|---|---|---|
| Sample | Initial % Purity | t = 1 week % Purity at 5° C. | Δ% Purity at 5° C. |
| H₂O | 95.58 | 94.66 | −0.92 |
| MeOH | 97.39 | 97.52 | +0.13 |
| ACN | 97.50 | 97.50 | 0.00 |
| IPA | 89.28 | 89.59 | +0.31 |
| pH 1* | — | — | — |
| pH 2* | — | — | — |
| pH 3* | — | — | — |
| pH 4* | — | — | — |
| pH 5* | — | — | — |
| pH 6 | 88.37 | 87.02 | −1.35 |
| pH 7 | 76.12 | 74.27 | −1.85 |
| pH 8 | 85.54 | 81.45 | −4.09 |
| pH 9 | 91.24 | 89.17 | −2.07 |

*Due to the low solubility of the pH 1-5 solutions, no stability data could be determined.

Compound 2 has demonstrated solubility and stability in selected aqueous buffers and organic solvents. For the solvents screened, Compound 2 was most soluble in MeOH, >50 mg/mL, the lowest solubility was in iso-propyl alcohol, 0.7 mg/mL. The pH solubility profile displayed an increase in solubility with an increase in pH. Compound 1 has a $pK_a$ of ~3.86 and this explains the pH solubility trend. The stability data obtained for the pH 1-5 samples gave inconclusive results due to the low solubility of Compound 2 in these buffers.

Example 15

Comparison of HPMC and Gelatin Capsules

Twenty capsules of both hydroxypropyl methylcellulose (HPMC, also known as Hypromellose) and gelatin were filled with 25±1 mg of amorphous Compound 2• to determine if the lower water content found in HPMC capsules would retard the water uptake of the compound. Samples of Compound 2 in both capsule types were placed at 25° C./60% RH and 40° C./75% RH for 1 week. The samples were analyzed for water content, potency, and % purity (% area) at t=0 and t=1 week.
Preparation of Compound 2 HPMC and Gelatin Samples
  20 transparent size 00 HPMC capsules and 20 transparent size 00 gelatin capsules were hand filled with API.
  Each capsules was filled with 25±1 mg of API.
  The two capsule types were both separated into two 30 cc HDPE bottles with caps and placed at both 25° C./60% RH and 40° C./75% RH for 1 week.
Sample Analysis at t=0
  For the t=0 time point, Compound 2 was analyzed for water content, potency, and % purity (% area).
Water Content
  Two samples of Compound 2 were taken at t=0 for water content. The first sample was taken after the HPMC capsules had been filled and the second sample was taken after the gelatin capsules had been filled. This sampling procedure was done to offset the water uptake that took place while the capsules were being filled.
  50.3 mg of Compound 2 was weighed into a crimp vial after the HPMC capsules had been filled.
  The vial was immediately crimped for Karl Fischer analysis.
  50.4 mg of Compound 2 was weighed into a crimp vial after the gelatin capsules had been filled.
  The vial was immediately crimped for Karl Fischer analysis.
Potency and % Purity (% Area)
  76.17 mg of Compound 2 was weighed directly into a 100-mL volumetric flask.
  The flask was diluted to volume with ACN and inverted to mix.
  A 1 mL aliquot was transferred directly into an HPLC vial for analysis.
  The samples were stored at 40° C./75% RH and 20° C./60% RH for 1 week and then samples were analyzed by HPLC for % purity and % potency. The results are shown in Table 28.

TABLE 28

HPMC vs. Gelatin Potency and Purity Results for t = 0 and t = 1 week

| Name | % Potency | % a/a Purity | Δ % a/a Purity |
|---|---|---|---|
| Sample t = 0 | 86.3 | 98.95 | N/A |
| HPMC Capsules, 25° C., t = 1 week | 90.2 | 98.95 | 0.00 |
| HPMC Capsules, 40° C., t = 1 week | 89.8 | 98.74 | −0.21 |
| Gelatin Capsules, 25° C., t = 1 week | 90.1 | 98.95 | 0.00 |
| Gelatin Capsules, 40° C., t = 1 week | 90.8 | 98.88 | −0.07 |

The HPMC vs. gelatin capsule comparison was implemented to determine if the lower starting water content of HPMC capsules would hinder the absorption of water by Compound 2. This experiment was also performed to learn if an increase in water content lead to a decrease in potency and % purity (% area) of the compound. The results showed that HPMC capsules did in fact slow the uptake of water, relative to gelatin, by 3.74% when stored at 40° C./75% RH. The potency and % purity (% area) of Compound 2 was unchanged for all conditions tested after 1 week.

Example 16

Particle Size Distribution, Powder Flow, Bulk Density, Tap Density and Milling Feasibility of Compound 2

Compound 2 particle size distribution was determined by sieve screen analysis. A sample of Compound 2 was passed through a series of sieves, which included a 53, 106, 250, 500, 710, and 1000 μm mesh screen. Each screen was weighed before and after the sieving occurred to determine the amount of compound at each particle size.

The powder flow was determined on a FlowDex apparatus.

Bulk density was determined by filling a tared 100 mL graduated cylinder with Compound 2. The volume and weight of Compound 2 added was recorded and used to calculate its bulk density. Tap density was then determined by taking the same graduated cylinder filled with Compound 2 and placing it on an Autotap set for 100 cycles. The new powder volume was recorded and used to calculate the tap density.

24.73 mg of Compound 2 was weighed directly into a tared 25 mL volumetric flask. The flask was diluted to volume with ACN and inverted to mix. A sample was taken to determine the % purity (% area) of the drug before milling took place. Milling was performed by taking 17.92 g of Compound 2 and passing this material it through a conical mill with an 1143 µm screen. 14.33 g of Compound 2 was recovered and re-analyzed for particle size distribution, bulk density, and tap density. 24.93 mg of milled Compound 2 was weighed directly into a tared 25 mL volumetric flask. The flask was diluted to volume with ACN and inverted to mix. This sample was taken to determine the % purity (% area) after Compound 2 had been milled. The results are shown in Tables 29, 30, 31 and 32.

TABLE 29

Bulk Compound 2 Particle Size Distribution

| Sieve Size (µm) | Wt. Compound 2 (mg) | % Wt. | % Undersized |
|---|---|---|---|
| 1000 | 1680.7 | 30.9 | 69.1 |
| 710 | 1355.2 | 24.9 | 44.2 |
| 500 | 1371.4 | 25.2 | 19.0 |
| 250 | 934.0 | 17.2 | 1.8 |
| 106 | 82.1 | 1.5 | 0.3 |
| 53 | 10.8 | 0.2 | 0.1 |
| <53 | 3.0 | 0.1 | 0.0 |
| Total Wt. | 5437.2 | | |

TABLE 30

Milled Compound 2 Particle Size Distribution (using 1143 µm screen)

| Sieve Size (µm) | Wt. Compound 2 (mg) | % Wt. | % Undersized |
|---|---|---|---|
| 1000 | 36.4 | 0.7 | 99.5 |
| 710 | 1258.8 | 23.5 | 76.0 |
| 500 | 1988.9 | 37.1 | 38.9 |
| 250 | 1691.5 | 31.6 | 7.3 |
| 106 | 335.8 | 6.3 | 1.0 |
| 53 | 40.9 | 0.8 | 0.2 |
| <53 | 8.2 | 0.2 | 0.0 |
| Total Wt. | 5360.5 | | |

TABLE 31

Bulk and Tap Density of Unmilled Compound 2

| Wt. Compound 2 | 8.86 g |
|---|---|
| Bulk Volume | 100 mL |
| Tapped Volume | 78 mL |
| Bulk Density | 0.089 g/mL |
| Tap Density | 0.114 g/mL |

TABLE 32

Bulk and Tap Density of Milled Compound 2

| Wt. Compound 2 | 7.27 g |
|---|---|
| Bulk Volume | 100 mL |
| Tapped Volume | 74 mL |
| Bulk Density | 0.073 g/mL |
| Tap Density | 0.098 g/mL |

% Purity of Compound 2 sample did not change with milling.

% Purity of Compound 2 sample did not change with milling.

After Compound 2 had been milled it was blended with 2.5% w/w of colloidal silicon dioxide, Cab-O—Sil®, on a T2 Turbula blender for 2 minutes. The blended powder was collected and its flow properties were analyzed on a FlowDex apparatus.

The powder flow of Compound 2 was determined on a FlowDex. The first condition tested was bulk unmilled Compound 2. The powder was unable to pass through the largest available, 34 mm, orifice. The second condition tested was milled Compound 2 that had been blended with 2.5% w/w colloidal silicon dioxide. The flow of the milled and blended Compound 2 passed through a 34 mm orifice but failed to pass through a 32 mm orifice.

Due to the low density and large particle size distribution of the bulk Compound 2, a milling process was used. The milling process lowered the average particle size of Compound 2 from ~775 µm to ~560 µm without degrading the drug. Milling the compound did however aerate the compound causing a decrease in bulk and tap density.

Example 17

Dissolution Comparison

Dissolution of three forms of solid sodium salt were analyzed, a monosodium trihydrate (Compound 6), a monosodium salt dihydrate (Compound 7) and amorphous Compound 2.

Preparation of Crystalline Trihydrate (Compound 6) Capsules

The crystalline material was made by exposing amorphous Compound 2 to ambient temperature/75% RH for 24 hrs. These conditions were created using a saturated sodium chloride solution sealed in a desiccant chamber. Once the crystalline material had been created it was collected and stored at 2-8° C. until dissolution testing took place. Two samples for dissolution were prepared by weighing 25 mg±1 mg into size 00 white opaque gelatin capsules.

Preparation of Crystalline Dihydrate (Compound 7) Capsules

Crystalline Compound 7 dihydrate was made by placing a sample of the iso-propanol solvate of Compound 2 at ambient temperature and humidity conditions for 2 weeks. The iso-propanol solvate of Compound 2 readily converts to the dihydrate. Once Compound 7 had been prepared, it was collected and stored at 2-8° C. until dissolution testing was conducted. Two samples for dissolution were prepared by weighing 25 mg±1 mg into size 00 white opaque gelatin capsules.

Preparation of Compound 2 Capsules

Two samples for dissolution were prepared by weighing 25 mg±1 mg of amorphous Compound 2 into size 00 white opaque gelatin capsules.

The dissolution materials and parameters are set out in Table 33. At each pull time ~6 mL of media was removed from each vessel and filtered through a 0.45 μm nylon filter. The first 5 mL of solution was discarded and the final 1 mL was collected in a UPLC vial for analysis.

TABLE 33

Dissolution Parameters and Materials.

| | |
|---|---|
| Dissolution Media | pH 6.8 Phosphate Buffer |
| Dissolution Media Volume per Vessel | 900 mL |
| Bath Temperature | 37.0 ± 0.5° C. |
| Paddle Speed | 50 RPM for 1st hour, 150 RPM for $2^{nd}$ hour |
| Pull Times | 15, 30, 45, 60, and 120 minutes |

The mean dissolution values at each time point for each sample were evaluated are provided in Table 34.

TABLE 34

Dissolution Results for Different Crystalline Forms of Compound 2

| Time (mins) | % Dissolution of Compound 7 | % Dissolution of Compound 6 | % Dissolution of Compound 2 |
|---|---|---|---|
| 15 | 72.8 | 39.4 | 77.8 |
| 30 | 74.7 | 56.5 | 83.6 |
| 45 | 77.4 | 64.4 | 86.3 |
| 60 | 78.2 | 69.6 | 88.8 |
| 120 | 80.9 | 88.9 | 92.9 |

As expected the crystalline forms of Compound 2 had the slowest dissolution rate, while amorphous Compound 2 dissolved considerably faster.

Example 18

Formulation

The components set out in Table 35 were mixed to provide a homogenous mixture and the mixture was placed in gelatin or HMPC capsules.

TABLE 35

Prototype formulations of amorphous Compound 2

| Component | Grade | 25 mg Formulation | 10 mg Formulation | 25 mg Formulation | 25 mg Formulation |
|---|---|---|---|---|---|
| Compound 2 | N/A | 6.49% | 6.49% | 6.49% | 5.06% |
| Colloidal Silicon Dioxide | Aerosil 200 Pharma (USP/NF, EP, JP) | 0.5% | 0.5% | 0.5% | 0.5% |
| Microcrystalline Cellulose (MCC) | Avicel PH102 (USP/NF, EP, JP) | 92.01% | 92.01% | 92.01% | — |
| Mannitol | Fast-Flo (USP/NF, EP, JP) | — | — | — | 93.44% |
| Magnesium Stearate | Vegetable Grade (USP/NF, EP, JP) | 1.0% | 1.0% | 1.0% | — |
| Stearic Acid | Hystyrene (USP/NF, EP, JP) | — | — | — | 1.0% |
| | Total | 100% | 100% | 100% | 100% |
| Capsule Shell Type | | HPMC (VCaps Plus) | HPMC (VCaps Plus) | Gelatin (Coni-Snap) | HPMC (VCaps Plus) |
| Capsule Fill Weight | | 440 mg | 176 mg | 440 mg | 565 mg |
| Capsule Size | | 00 | 2 | 00 | 00 |

Stability of selected 25 mg formulations is shown at one month at 40° C./75° C. RH in Table 36.

TABLE 36

Stability.

| | HMPC/Mannitol | | HPMC/MCC | | Gelatin/MCC | |
|---|---|---|---|---|---|---|
| | initial | one month | initial | one month | initial | one month |
| Appearance | white opaque 00 capsule white/off white powder | No change | white opaque 00 capsule white/off white powder | No change | white opaque 00 capsule white/off white powder | No change |
| Assay | 100.1% | 95.4% | 98.0% | 95.4% | 97.4% | 96.8% |
| Related substances | 0.20% | 1.26% | 0.27% | 0.7% | 0.24% | 0.57% |
| Water content | 1.13% | 1.56% | 5.52% | 5.92% | 6.53% | 7.13% |

Example 19

Preparation of Compound 2 from Free Acid Compound 1

Compound 1 (31.35 g, 61.8 mmol, 95.82% purity) was dissolved in dichloromethane (DCM) (150 mL) and treated with sodium ethoxide solution (20.05 mL, 21% w/w). The mixture was evaporated to dryness and then dissolved in ethyl acetate (110 mL). To this solution was added iso-propanol (315 mL) dropwise with stirring causing rapid crystallization. Twenty minutes after complete addition of iso-propanol, the crystals were filtered, washed with iso-propanol (80 mL) and dried on the sinter for approximately 3 h. this gave 28.71 g cream powder. This material was dissolved in 290 mL of distilled water with warming (40° C.) and stirred at ambient temperature for 1 h with resulting crystallization. The mixture was filtered and the residue dried under vacuum giving 21.35 g (65%) white solid. HPLC analysis revealed the material was >98% e.e. and in 99.3% purity.

m/z (ES) 506.2 [MH$^+$, 100%], 507.2 [13C$_1$-MH$^+$, 40%]; HRMS C$_{32}$H$_{28}$NO$_5$ requires 506.1969. found 506.1967; $^1$H NMR (CDCl$_3$, 300 MHz) δ 2.08 (1H*, dd, J 16.6, 6.4), 2.83 (1H, dd, J 15.9, 6.4), 3.03 (1H, dd, J 15.9, 6.4), 3.36 (1H*, m), 3.55 (3H*, s), 3.66 (3H, s), 4.29-4.47 (3H, 2H*, m), 4.68 (1H*, d, J 11.0, 4.83 (2H, m), 4.83 (1H*, m), 4.91 (1H*, d, J 17.0, 5.28 (1H*, s), 5.31 (1H, s), 6.21 (1H, d, J 8.3), 6.46 (1H, d, J 8.3), 6.48 (1H*, d, J 8.3), 6.94-7.32 (15H, m); $^{13}$C NMR (CDCl$_3$, 500 MHz) δ 25.5 (CH$_2$), 26.0 (*CH$_2$), 42.8 (*CH$_2$), 45.8 (CH$_2$), 55.0, 55.8, 56.1, 56.7, 74.2 (*CH$_2$), 74.9 (CH$_2$), 110.2 (CH), 110.7 (*CH), 121.1 (CH), 122.0 (*CH), 126.4, 126.7, 126.8, 127.0, 127.8, 127.9, 128.3, 128.5, 128.6, 128.7, 128.8, 129.0, 129.5, 129.5, 129.8, 137.5 (q), 127.7 (*q), 139.3 (q), 139.3 (*q), 139.9 (q), 140.7 (*q), 144.4 (q), 144.7 (*q) 150.7 (*q), 151.6 (q), 172.2 (q), 172.7 (*q), 177.7 (q); [α]$_D^{25}$=−39.1 (CH$_2$Cl$_2$, c0.68); IR (cm$^{-1}$, KBr disc) 3425 (O—H), 1626 (C=O), 1601 (C=O). * denotes the minor rotomer.

Example 20

Acylation of Isoquinoline and Crystallization

Acylation Step

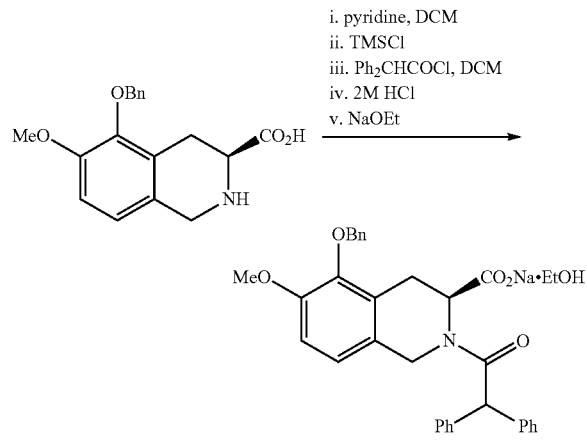

A suspension of dichloromethane (DCM), isoquinoline (1.0 eq) and pyridine (6.0 eq) was cooled to −12±2° C. under an inert nitrogen atmosphere. Chlorotrimethylsilane (4.0 eq) was added gradually to the suspension while maintaining an internal temperature of −10° C. or less. After complete addition an approximately homogeneous solution will result. The reaction mixture was agitated for a minimum of 20 minutes and the internal temperature adjusted to −12±2° C. A DCM solution of diphenylacetyl chloride (0.9 eq) was then added gradually to the reaction mixture while maintaining an internal temperature of less than −10° C. The reaction mixture was stirred for a minimum of 15 mins following complete addition while maintaining an internal temperature of less than −10° C.

The reaction was quenched with 2M hydrochloric acid and the mixture warmed to +20±5° C. Agitation was stopped and the biphasic mixture was left to settle for a minimum of 15 minutes. The lower (organic) phase was separated. Sodium ethoxide solution (21% in ethanol, 1.0 eq) was added to the organic phase and the resulting solution was evaporated to give the sodium salt ethanol solvate Compound 4.

Crystallization Step

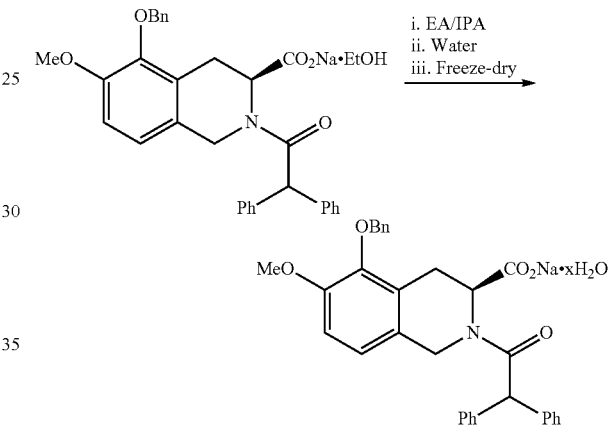

The crude sodium salt ethanol solvate Compound 4 was dissolved in ethyl acetate (EA) and then concentrated. The residue was dissolved in ethyl acetate and then stirred at +20±5° C. Isopropanol was added gradually in a controlled addition to the stirred ethyl acetate solution. This causes crystallization of the iso-propanol solvate, Compound 5. Following complete addition the mixture was stirred for one hour. The crystals were filtered and washed with iso-propanol. The crystals were dried under vacuum until iso-propanol levels are less than 10%. The crystals were added to a stirred volume of RO water causing rapid dissolution to occur. The resulting solution was stirred for two hours allowing a thick precipitate to form. The resulting slurry was then freeze-dried giving Compound 2 as an off-white powder.

Example 21

Pyrazole Active Ester Formation

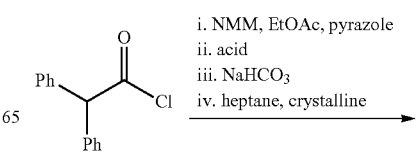

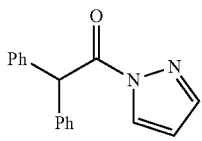

A glass or stainless steel jacketed vessel was placed under an inert atmosphere. To the vessel were charged pyrazole (1.1 eq), N-methylmorpholine (NMM) (1.3 eq) and ethyl acetate. An ethyl acetate solution of diphenylacetyl chloride (1.0 eq) was added gradually. Cooling of the reaction vessel was applied so as to maintain an internal temperature below +30° C. Following complete addition the contents were stirred for a minimum of 20 minutes. The reaction mixture was washed with water, 1M sulphuric acid (2×), saturated aqueous sodium bicarbonate (2×), water and brine. The ethyl acetate phase was concentrated and the residue was stripped with heptane.

The residue was heated to 70° C. in heptane so as to dissolve all solids. The resulting solution was cooled and held at 15±5° C. for 1 h with concomitant crystallization. The crystals were filtered and dried for a minimum of 16 h. Yield: 80-90% from diphenylacetyl chloride.

Isoquinoline Acylation

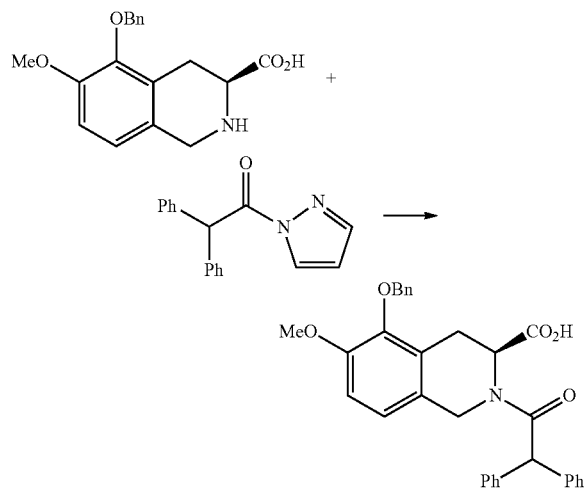

A glass lined or stainless steel vessel was placed under an inert atmosphere. To the vessel was charged DMF, tetramethylguanidine (1.03 eq) and isoquinoline (1.0 eq). The mixture was stirred for approximately 1 h to allow dissolution to occur (only partial dissolution was expected at this stage). To the reaction mixture was charged pyrazole active ester (1.2 eq). The reaction mixture was stirred for a minimum of 16 h. An IPC (HPLC) was performed to verify the extent of reaction (pass condition: <5.00% isoquinoline remaining). Dimethylethylenediamine (0.3 eq) was charged to the reaction mixture and stirring continued for a further 2 h. An IPC(HPLC) was performed for pyrazole active ester (pass condition: <0.10% pyrazole active ester).

The reaction mixture was diluted with toluene and washed with 1M sulfuric acid (2×) and water (2×). The organic phase was reduced in volume through evaporation of solvent. Sodium ethoxide (1.0 eq) was charged to the reaction mixture. The remaining solvent was evaporated from the reaction mixture. The residue was evaporated from ethyl acetate.

The crude product was agitated in ethyl acetate and the mixture transferred to a stirred vessel. Iso-propanol was charged to the ethyl acetate solution in a controlled addition causing crystallization to occur. The mixture was stirred for a minimum of 1 h. The crystals were filtered and washed with a small volume of iso-propanol. The crystals were dried under vacuum for a minimum of 16 h giving Compound 5.

Water was charged to a glass lined or stainless steel vessel. The internal temperature was adjusted to 40±2° C. The crystals of Compound 5 were slowly charged to the water, allowing dissolution to occur. The warm solution was dispensed in to lyoguard trays and loaded in to the freeze-dryer. Primary drying was conducted with a shelf temperature of −5° C. over at least 3 days. The secondary drying phase is conducted with a shelf temperature of +25° C. over at least 24 h. An IPC (KF) was performed to verify acceptable water content (pass condition: <15.0% water). Compound 2 was removed from the lyoguard trays and placed in appropriate containment. Yield: 80-90% from isoquinoline.

Example 22

Bioavailablility of Compound 2

Compound 2 in HPMC capsules was orally administered in varying amounts, 10 mg, 25 mg, 50 mg, 100 mg and 200 mg, once a day for seven days to healthy male subjects (18-55 years of age).

Blood samples were taken at regular intervals following each dose and the plasma derived from the blood samples analyzed for levels of Compound 1. The data obtained was used to calculate pharmacological parameters as shown in Table 37.

TABLE 37

Pharmacological parameters for Compound 2

| | Mean (SD) by Cohort | | | | | |
|---|---|---|---|---|---|---|
| Dose (mg) | $T_{max}$ (hr) | $C_{max}$ (ng/mL) | $AUC_{0-24}$ (hr*ng/mL) | $K_{el}$ (1/hr) | $T_{1/2}$ (hr) | $AUC_{0-\infty}$ (hr*ng/mL) |
| 10 | 1.10 (0.74) | 34.5 (18.3) | 66.4 (22.2) | 0.123 (0.071) | 8.05 (5.31) | 69.9 (24.4) |
| | n = 15 | n = 15 | n = 15 | n = 15 | n = 15 | n = 15 |
| 25 | 1.50 (0.89) | 112.6 (78.2) | 194.6 (72.5) | 0.079 (0.029) | 10.68 (6.56) | 223.8 (60.0) |
| | n = 8 | n = 8 | n = 8 | n = 7 | n = 7 | n = 7 |
| 50 | 1.0 (0.84) | 207.6 (101.8) | 334.5 (83.6) | 0.075 (0.044) | 13.44 (9.40) | 353.5 (78.4) |
| | n = 6 | n = 6 | n = 6 | n = 6 | n = 6 | n = 6 |
| 100 | 1.29 (0.95) | 451.3 (310.2) | 720.9 (181.1) | 0.066 (0.017) | 11.20 (3.21) | 758.7 (171.0) |
| | n = 7 | n = 7 | n = 7 | n = 7 | n = 7 | n = 7 |
| 200 | 1.14 (0.63) | 589.0 (367.0) | 1307.5 (572.3) | 0.073 (0.038) | 13.15 (9.43) | 1369.1 (583.7) |
| | n = 7 | n = 7 | n = 7 | n = 7 | n = 7 | n = 7 | n = number of subjects at each dose level.

Example 23

Pharmakokinetic Analysis of Compounds 2 (Amorphous), 6, 7 and 1 in Male Beagle Dogs Following a Single Oral Dose The study was designed to compare the PK profiles of the following four forms of Compound 1 administered as single oral capsules in fasted state. The randomization schedule for the animals is summarized in the table below. Briefly, the study consisted of 4 male dogs; each received single 10 mg/kg doses of each of the four compounds: Compound 2 sodium salt amorphous, Compound 6, Compound 7 and Compound 1 free carboxylic acid. There was a washout period of 4 days between dosing. The blood samples were collected from each animal at predetermined times on the study Days 1, 4, 8 and 11. The plasma was analyzed for Compound 1 by a validated HPLC-MS/MS assay.

| Animal | Day 1 | Day 4 | Day 8 | Day 11 |
|---|---|---|---|---|
| 1 | A | D | C | B |
| 2 | B | A | D | C |
| 3 | C | B | A | D |
| 4 | D | C | B | A |

A - Compound 2 (Amorphous)
B - Compound 6
C - Compound 7
D - Compound 1

Descriptive PK parameters were determined by standard model independent methods (Gibaldi and Perrier, 1982) based on the individual plasma concentration-time data. Plasma concentrations were rounded to 3 significant figures. Plasma samples with concentrations below the quantifiable assay limit (BQL<2.00 ng/mL) were assigned values of zero for mean calculations. For PK calculations, BQL was set to zero from the pre-dose time up to the time of the first quantifiable concentration and thereafter was set as missing. Nominal time points were used for all calculations.

Cmax is the observed maximum plasma concentration after dosing.

Tmax is the time to reach Cmax.

$T_{1/2}$ is apparent half-life calculated by $\ln(2)/\lambda$ where $\lambda$ is the rate constant for the log-linear portion of the terminal phase. A minimum of three values in the post-distribution phase of the plasma concentration-time curve is required for calculation of $\lambda$.

AUC(0-T) is the area under the plasma concentration-time curve from time zero to the time of the last measurable plasma concentration determined using the linear trapezoidal rule.

AUC(0-inf) is the area under the plasma concentration-time curve from time zero to infinity. It is calculated by summing AUC(0-T) and the extrapolated area from the T to infinity.

PK analyses were performed by noncompartmental analysis using model 200 in WinNonlin Professional 6.1 (Pharsight Corp., Mountain View, Calif.).

Individual, mean and SD values for Compound 1 plasma concentrations and PK parameters following Compound 2 (amorphous), Compound 6, Compound 7 and Compound 1 free carboxylic acid are presented in Tables 38, 39, 40 and 41, respectively. Compound 1 mean PK parameters are summarized in Table 42. Compound 1 Mean plasma concentration-time profiles following different forms are shown in FIG. 11 and the mean Cmax and AUC(O-inf) are presented in FIG. 12.

Following a single oral dose of Compound 1 at 10 mg/kg, the median Tmax values were 0.750, 1.00, 1.00 and 2.00 hours for Compound 2 sodium salt amorphous, Compound 6, Compound 7 and Compound 1 free carboxylic acid, respectively (Table 42). The corresponding mean Cmax values were 1590±534, 1320±1050, 1260±428 and 294±238 ng/mL, respectively (Table 42). Mean AUC(O-inf) values were 1840±516, 1930±1240, 2440±542 and 680±412 ng·h/mL, respectively. The AUC following Compound 6 and free carboxylic acid had higher inter-subject variability than the Compound 2 amorphous and Compound 7 hydrate (% CV values ranging from 60.6% to 81.1%; see Table 42). The Compound 7 hydrate resulted in the highest mean AUC while the free carboxylic acid Compound 1 resulted in the lowest AUC. Mean harmonic $T_{1/2}$ values were 2.49±0.391, 2.82±1.18, 4.36±3.16 and 2.11±0.115 hours for Compound 2 sodium salt amorphous, Compound 6, Compound 6 and free carboxylic acid Compound 1, respectively (FIG. 11 and Table 42).

The longest Tmax was observed following the free carboxylic acid Compound 1 at a median value of 2 hours compared with 0.75 to 1 hour for Compound 2 (amorphous), Compound 6, and Compound 7. The highest mean Cmax value was observed following Compound 2 (amorphous) (1590±534 ng/mL) and the highest mean AUC value was observed following Compound 6 (2440±542 ng·h/mL).

TABLE 38

Plasma Concentrations (ng/mL) and PK Parameters of Compound 1 in Dogs Following a Single Oral 10 mg/kg Dose of Compound 2 Amorphous Form

| Parameter | Time (h) | Dog I.D. 301 | 302 | 303 | 304 | N | Mean | SD | % CV |
|---|---|---|---|---|---|---|---|---|---|
| | Predose | BQL | BQL | BQL | BQL | 4 | 0.00 | 0.00 | NA |
| | 0.25 | BQL | BQL | BQL | 26.5 | 4 | 6.63 | 13.3 | 200 |
| | 0.5 | 597 | 14.1 | BQL | 2,270 | 4 | 720 | 1,070 | 149 |
| | 0.75 | 1,110 | 146 | 1,750 | 1,090 | 4 | 1,020 | 661 | 64.5 |
| | 1 | 830 | 1,220 | 835 | 880 | 4 | 941 | 187 | 19.9 |
| | 2 | 148 | 763 | 195 | 345 | 4 | 363 | 280 | 77.1 |
| | 4 | 25.5 | 48.6 | 44.4 | 54.1 | 4 | 43.2 | 12.4 | 28.8 |
| | 8 | 9.07 | 19.4 | 16.4 | 23.1 | 4 | 17.0 | 5.95 | 35.0 |
| | 12 | 2.81 | 6.39 | 2.95 | 7.53 | 4 | 4.92 | 2.40 | 48.8 |
| | 24 | BQL | 20.7 | 6.83 | BQL | 4 | 6.88 | 9.76 | 142 |
| Tmax[a], h | | 0.750 | 1.00 | 0.750 | 0.500 | 4 | 0.750 | 0.5-1 | 27.2 |
| Cmax, ng/mL | | 1,110 | 1,220 | 1,750 | 2,270 | 4 | 1,590 | 534 | 33.6 |
| AUC(0-T), ng · h/mL | | 1,290 | 2,350 | 1,520 | 2,180 | 4 | 1,830 | 512 | 27.9 |
| AUC(0-inf), | | | | | | | | | |

TABLE 38-continued

Plasma Concentrations (ng/mL) and PK Parameters of Compound 1 in Dogs
Following a Single Oral 10 mg/kg Dose of Compound 2 Amorphous Form

| Parameter | Time (h) | 301 | 302 | 303 | 304 | N | Mean | SD | % CV |
|---|---|---|---|---|---|---|---|---|---|
| ng · h/mL |  | 1,300 | 2,350 | 1,520 | 2,220 | 4 | 1,840 | 516 | 28.0 |
| $T_{1/2}^{b}$, h |  | 2.51 | 2.73 | 2.05 | 2.81 | 4 | 2.49 | 0.391 | 15.7 |

[a]Expressed as median and range
[b]Expressed as harmonic mean and pseudo SD
BQL—Below the Quantifiable Limit <2.00 ng/mL
NA—Not Applicable

TABLE 39

Plasma Concentrations (ng/mL) and PK Parameters of Compound
1 in Dogs Following a Single Oral 10 mg/kg Dose of Compound 6

| Parameter | Time (h) | 301 | 302 | 303 | 304 | N | Mean | SD | % cv |
|---|---|---|---|---|---|---|---|---|---|
|  | Predose | BQL | BQL | BQL | BQL | 4 | 0.00 | 0.00 | NA |
|  | 0.25 | BQL | 313 | BQL | 1,180 | 4 | 373 | 558 | 149 |
|  | 0.5 | BQL | 255 | 8.80 | 2,560 | 4 | 706 | 1,240 | 176 |
|  | 0.75 | 5.31 | 588 | 180 | 1,520 | 4 | 573 | 677 | 118 |
|  | 1 | 27.7 | 1,790 | 252 | 857 | 4 | 732 | 788 | 108 |
|  | 2 | 658 | 1,170 | 160 | 161 | 4 | 537 | 483 | 89.8 |
|  | 4 | 55.2 | 52.0 | 24.0 | 70.9 | 4 | 50.5 | 19.5 | 38.6 |
|  | 8 | 9.17 | 12.0 | 12.1 | 12.8 | 4 | 11.5 | 1.60 | 13.9 |
|  | 12 | 4.50 | 5.90 | 4.11 | 5.68 | 4 | 5.05 | 0.877 | 17.4 |
|  | 24 | BQL | 2.00 | 10.3 | BQL | 4 | 3.08 | 4.91 | 159 |
| $Tmax^{a}$, h |  | 2.00 | 1.00 | 1.00 | 0.500 | 4 | 1.00 | 0.5-2 | 55.9 |
| Cmax, ng/mL |  | 658 | 1,790 | 252 | 2,560 | 4 | 1,320 | 1,050 | 80.2 |
| AUC(0-T), ng · h/mL |  | 1,220 | 3,430 | 660 | 2,370 | 4 | 1,920 | 1,230 | 64.2 |
| AUC(0-inf), ng · h/mL |  | 1,230 | 3,440 | 661 | 2,380 | 4 | 1,930 | 1,240 | 64.2 |
| $T_{1/2}^{b}$, h |  | 2.21 | 6.48 | 3.14 | 2.03 | 4 | 2.82 | 1.18 | 41.8 |

[a]Expressed as median and range
[b]Expressed as harmonic mean and pseudo SD
BQL—Below the Quantifiable Limit <2.00 ng/mL
NA—Not Applicable

TABLE 40

Plasma Concentrations (ng/mL) and PK Parameters of Compound
1 in Dogs Following a Single Oral 10 mg/kg Dose of Compound 6

| Parameter | Time (h) | 301 | 302 | 303 | 304 | N | Mean | SD | % CV |
|---|---|---|---|---|---|---|---|---|---|
|  | Predose | BQL | BQL | BQL | BQL | 4 | 0.00 | 0.00 | NA |
|  | 0.25 | 2.72 | BQL | 10.0 | BQL | 4 | 3.18 | 4.72 | 149 |
|  | 0.5 | 16.1 | 199 | 813 | 83.2 | 4 | 278 | 365 | 131 |
|  | 0.75 | 512 | 372 | 415 | 672 | 4 | 493 | 133 | 27.0 |
|  | 1 | 1,060 | 269 | 857 | 1,850 | 4 | 1,010 | 653 | 64.8 |
|  | 2 | 792 | 1,270 | 428 | 932 | 4 | 856 | 349 | 40.7 |
|  | 4 | 67.9 | 60.1 | 49.0 | 83.5 | 4 | 65.1 | 14.5 | 22.3 |
|  | 8 | 16.9 | 15.2 | 10.2 | 18.1 | 4 | 15.1 | 3.48 | 23.0 |
|  | 12 | 5.79 | 4.22 | 6.63 | 8.07 | 4 | 6.18 | 1.61 | 26.0 |
|  | 24 | 3.56 | 2.75 | 3.21 | BQL | 4 | 2.38 | 1.62 | 68.1 |
| $Tmax^{a}$, h |  | 1.00 | 2.00 | 1.00 | 1.00 | 4 | 1.00 | 1-2 | 40.0 |
| Cmax, ng/mL |  | 1,060 | 1,270 | 857 | 1,850 | 4 | 1,260 | 428 | 34.0 |
| AUC(0-T), ng · h/mL |  | 2,320 | 2,510 | 1,750 | 3,080 | 4 | 2,410 | 550 | 22.8 |
| AUC(0-inf), ng · h/mL |  | 2,340 | 2,520 | 1,790 | 3,110 | 4 | 2,440 | 542 | 22.2 |
| $T_{1/2}^{b}$, h |  | 5.21 | 4.93 | 9.97 | 2.37 | 4 | 4.36 | 3.16 | 72.5 |

[a]Expressed as median and range
[b]Expressed as harmonic mean and pseudo SD
BQL—Below the Quantifiable Limit <2.00 ng/mL
NA—Not Applicable

TABLE 41

Plasma Concentrations (ng/mL) and PK Parameters of Compound 1 in Dogs Following a Single Oral 10 mg/kg Dose of Compound 1 in Free Carboxylic Acid Form

| Parameter | Time (h) | Dog I.D. 301 | 302 | 303 | 304 | N | Mean | SD | % CV |
|---|---|---|---|---|---|---|---|---|---|
| | Predose | BQL | BQL | BQL | BQL | 4 | 0.00 | 0.00 | NA |
| | 0.25 | BQL | 3.55 | BQL | BQL | 4 | 0.888 | 1.78 | 200 |
| | 0.5 | 15.9 | 5.52 | BQL | BQL | 4 | 5.36 | 7.50 | 140 |
| | 0.75 | 40.2 | 5.18 | BQL | BQL | 4 | 11.3 | 19.4 | 171 |
| | 1 | 139 | 8.08 | 2.32 | 81.4 | 4 | 57.7 | 65.1 | 113 |
| | 2 | 38.3 | 392 | 62.1 | 582 | 4 | 269 | 264 | 98.3 |
| | 4 | 16.1 | 35.0 | 29.7 | 29.6 | 4 | 27.6 | 8.07 | 29.2 |
| | 8 | 5.44 | 11.3 | 5.88 | 5.83 | 4 | 7.11 | 2.80 | 39.3 |
| | 12 | BQL | 2.15 | BQL | 2.31 | 4 | 1.12 | 1.29 | 115 |
| | 24 | BQL | BQL | BQL | BQL | 4 | 0.00 | 0.00 | NA |
| $T_{max}^a$, h | | 1.00 | 2.00 | 2.00 | 2.00 | 4 | 2.00 | 1-2 | 28.6 |
| Cmax, ng/mL | | 139 | 392 | 62.1 | 582 | 4 | 294 | 238 | 81.1 |
| AUC(0-T), ng · h/mL | | 218 | 751 | 195 | 1,040 | 4 | 551 | 415 | 75.3 |
| AUC(0-inf), ng · h/mL | | 234 | 758 | ND | 1,050 | 3 | 680 | 412 | 60.7 |
| $T_{1/2}^b$, h | | 2.18 | 1.99 | ND | 2.17 | 3 | 2.11 | 0.115 | 5.45 |

$^a$Expressed as median and range
$^b$Expressed as harmonic mean and pseudo SD
BQL—Below the Quantifiable Limit <2.00 ng/mL
NA—Not Applicable
ND—Not Determined

TABLE 42

Summary of Mean PK Parameters of Compound 1 in Dogs Following Compound 1, Compound 2 (Amorphous), Compound 6, and Compound 7

| Compound Administered | Statistic | $T_{max}^a$ (h) | Cmax (ng/mL) | AUC(0-T) (ng · h/mL) | AUC(0-inf) (ng · h/mL) | $T_{1/2}^b$ (h) |
|---|---|---|---|---|---|---|
| Compound 2 | N | 4 | 4 | 4 | 4 | 4 |
| Sodium Salt | Mean | 0.750 | 159 | 1,840 | 1,840 | 2.49 |
| Amorphous | SD | 0.5-1 | 53.4 | 515 | 516 | 0.391 |
| | CV % | 27.2 | 33.6 | 28.0 | 28.0 | 15.7 |
| Compound 6 | N | 4 | 4 | 4 | 4 | 4 |
| | Mean | 1.00 | 132 | 1,920 | 1,930 | 2.82 |
| | SD | 0.5-2 | 105 | 1,230 | 1,240 | 1.18 |
| | CV % | 55.9 | 80.2 | 64.0 | 64.2 | 41.8 |
| Compound 7 | N | 4 | 4 | 4 | 4 | 4 |
| | Mean | 1.00 | 126 | 2,420 | 2,440 | 4.36 |
| | SD | 1-2 | 42.8 | 561 | 542 | 3.16 |
| | CV % | 40.0 | 34.0 | 23.2 | 22.2 | 72.5 |
| Compound 1 | N | 4 | 4 | 3 | 3 | 3 |
| | Mean | 2.00 | 29.4 | 680 | 680 | 2.11 |
| | SD | 1-2 | 23.8 | 412 | 412 | 0.115 |
| | CV % | 28.6 | 81.1 | 60.6 | 60.7 | 5.45 |

$^a$Expressed as median and range
$^b$Expressed as harmonic mean and pseudo SD

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims.

What is claimed:

1. The sodium salt of (S)-2-(diphenylacetyl)-1,2,3,4-tetrahydro-6-methoxy-5-(phenylmethoxy)-3-isoquinoline carboxylic acid wherein the sodium salt is a non-solvated crystalline form that exhibits an XRPD pattern comprising at least one peak at about 9.6 degrees 2θ.

2. The compound of claim 1 wherein said crystalline form exhibits an XRPD pattern further comprising at least one peak selected from the group consisting of about 6.0 and 19.6 degrees 2θ.

3. The compound of claim 2 wherein said crystalline form exhibits an XRPD pattern further comprising at least one peak selected from the group consisting of about 14.0 17.9, 20.6, 21.8, 23.3, and 23.9 degrees 2θ.

4. The compound of claim 3 wherein said crystalline form exhibits an XRPD pattern substantially the same as FIG. 1.

5. The compound of claim 4 wherein said crystalline form exhibits an XRPD pattern comprising peaks at 2θ equal to 5.5, 6.0, 6.9, 8.5, 9.6, 11.0, 13.3, 14.0, 16.1, 16.7, 17.9, 18.4, 19.6, 20.6, 21.8, 22.3, 23.3, 23.9, 25.5, 26.3, and 27.6.

6. A pharmaceutical composition comprising the sodium salt of (S)-2-(diphenylacetyl)-1,2,3,4-tetrahydro-6-methoxy-5-(phenylmethoxy)-3-isoquinoline carboxylic acid wherein the sodium salt is a non-solvated crystalline form that exhibits an XRPD pattern comprising at least one peak at about 9.6 degrees 2θ together with a pharmaceutically acceptable carrier, diluent or excipient.

7. The pharmaceutical composition of claim 6 formulated for oral delivery.

8. The pharmaceutical composition of claim 6 wherein said crystalline form exhibits an XRPD pattern further comprising at least one peak selected from the group consisting of about 6.0 and 19.6 degrees 2θ.

9. The pharmaceutical composition of claim 8 wherein said crystalline form exhibits an XRPD pattern further comprising at least one peak selected from the group consisting of about 14.0 17.9, 20.6, 21.8, 23.3, and 23.9 degrees 2θ.

10. The pharmaceutical composition of claim 9 wherein said crystalline form exhibits an XRPD pattern substantially the same as FIG. 1.

11. The pharmaceutical composition of claim 10 wherein said crystalline form exhibits an XRPD pattern comprising peaks at 2θ equal to 5.5, 6.0, 6.9, 8.5, 9.6, 11.0, 13.3, 14.0, 16.1, 16.7, 17.9, 18.4, 19.6, 20.6, 21.8, 22.3, 23.3, 23.9, 25.5, 26.3, and 27.6.

* * * * *